US007868177B2

(12) United States Patent
Cee et al.

(10) Patent No.: US 7,868,177 B2
(45) Date of Patent: Jan. 11, 2011

(54) MULTI-CYCLIC COMPOUNDS AND METHOD OF USE

(75) Inventors: Victor J. Cee, Thousand Oaks, CA (US); Holly L. Deak, Brookline, MA (US); Stephanie D. Geuns-Meyer, Medford, MA (US); Brian L. Hodous, Cambridge, MA (US); Hanh Nho Nguyen, Arlington, MA (US); Philip R. Olivieri, Medford, MA (US); Vinod F. Patel, Acton, MA (US); Karina Romero, Cambridge, MA (US)

(73) Assignee: Amgen Inc., Thousand Oaks, CA (US)

(*) Notice: Subject to any disclaimer, the term of this patent is extended or adjusted under 35 U.S.C. 154(b) by 363 days.

(21) Appl. No.: 11/709,994

(22) Filed: Feb. 21, 2007

(65) Prior Publication Data

US 2007/0213325 A1 Sep. 13, 2007

Related U.S. Application Data

(60) Provisional application No. 60/776,507, filed on Feb. 24, 2006.

(51) Int. Cl.

| | |
|---|---|
| ***C07D 401/14*** | (2006.01) |
| ***C07D 403/14*** | (2006.01) |
| ***A61K 31/4427*** | (2006.01) |
| ***A61K 31/506*** | (2006.01) |
| ***A61K 31/53*** | (2006.01) |
| ***A61P 19/02*** | (2006.01) |
| ***A61P 35/00*** | (2006.01) |

(52) U.S. Cl. .................... 546/268.1; 546/288; 514/341; 514/345; 514/269; 514/275; 514/241; 544/242; 544/180

(58) Field of Classification Search .............. 544/268.1, 544/288, 242; 514/341, 345, 269, 275; 546/268.1, 546/288

See application file for complete search history.

(56) References Cited

U.S. PATENT DOCUMENTS

| | | | | |
|---|---|---|---|---|
| 6,143,764 | A | 11/2000 | Kubo | |
| 6,919,338 | B2 | 7/2005 | Mortlock | |
| 2007/0185324 | A1* | 8/2007 | De Morin et al. | 544/60 |

FOREIGN PATENT DOCUMENTS

| | | | |
|---|---|---|---|
| WO | 0047212 | A1 | 8/2000 |
| WO | 0232872 | A1 | 4/2002 |
| WO | 03055491 | A1 | 7/2003 |
| WO | 2004000833 | A1 | 12/2003 |
| WO | 2004016612 | A2 | 2/2004 |
| WO | 03000660 | A3 | 4/2004 |
| WO | 2004037814 | A1 | 5/2004 |
| WO | 2004039774 | A2 | 5/2004 |
| WO | 2005033086 | A1 | 4/2005 |
| WO | 2005042520 | A1 | 5/2005 |
| WO | 2005113494 | A2 | 12/2005 |

OTHER PUBLICATIONS

Wolff Manfred E. "Burger's Medicinal Chemistry, 5ed, Part 1", John Wiley & Sons, 1995, pp. 975-977.*

Banker, G.S. et al, "Modern Pharmaceutices, 3ed.", Marcel Dekker, New York. 1996, pp. 451 and 596.*

West, Anthony R., Solid State Chemistry and its Applications, Wiley, New York, 1988, pp. 358 & 365.*

Vippagunta et al., Advanced Drug Delivery Reviews 48: 3-26, 2001.*

Cecil Textbook of Medicine, edited by Bennet, J.C., and Plum F., 20th edition,vol. 1, 1004-1010, 1996.*

Mass, R. D., Int. J. Radiation Oncology Bio. Phys.vol. 58(3): 932-940, 2004.*

Fabbro et al. Pharmacology & therapeutics 93, 79-98, 2002.*

De Morin et al., US 2007/0185324; CA 147: 143458, 2007; CAPLUS Abstract.*

U.S. Appl. No. 12/639,931.

U.S. Appl. No. 12/619,573.

Y. Miyoshi et al., Int. J. Cancer, 92:370-373 (2001).

* cited by examiner

*Primary Examiner*—Venkataraman Balasubramanian
(74) *Attorney, Agent, or Firm*—G. Prabhakar Reddy

(57) ABSTRACT

The present invention relates to chemical compounds having a general formula I

I

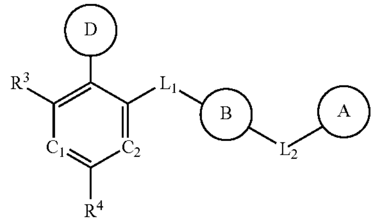

wherein A, B, $C^1$, $C^2$, D, $L^1$, $L^2$ and $R^{3-4}$ are defined herein, and synthetic intermediates, which are capable of modulating various protein kinase receptor enzymes and, thereby, influencing various disease states and conditions related to the activities of such kinases. For example, the compounds are capable of modulating Tie-2 and Aurora kinase enzymes thereby influencing angiogenesis and the process of cell cycle and cell proliferation, respectively, to treat cancer and cancer-related diseases. The invention also includes pharmaceutical compositions, including the compounds, and methods of treating disease states related to the activity of various protein kinases.

22 Claims, No Drawings

MULTI-CYCLIC COMPOUNDS AND METHOD OF USE

This application claims the benefit of U.S. Provisional Application No. 60/776,507, filed Feb. 24, 2006, which is hereby incorporated herein by reference in its entirety.

FIELD OF THE INVENTION

The invention relates to the field of pharmaceutical agents and, more specifically, to multi-cyclic compounds, compositions, uses and methods for treating oncological disorders, including cancer.

BACKGROUND OF THE INVENTION

Protein kinases play a central role in the regulation and maintenance of a wide variety of cellular processes and cellular function. For example, kinase activity acts as molecular switches regulating cell proliferation, activation, and/or differentiation and cell-cycling processes. Uncontrolled or excessive kinase activity has been observed in many disease states including benign and malignant proliferative disorders as well as diseases resulting from inappropriate activation of various cellular processes. In addition, endothelial cell specific receptor protein tyrosine kinases, such as Tie-2, mediate the angiogenic process and are, therefore, involved in supporting the progression of cancers and other diseases involving uncontrolled vascularization.

The ability to regulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Regulating angiogenesis by inhibiting certain recognized pathways in this process would therefore, be useful in treating diseases, such as ocular neovascularization, including retinopathies (including diabetic retinopathy), age-related macular degeneration, psoriasis, hemangioblastoma, hemangioma, arteriosclerosis, inflammatory disease rheumatoid arthritis, chronic inflammatory disorders such as chronic asthma, arterial or post-transplantational atherosclerosis, endometriosis, and neoplastic diseases such as leukemias, otherwise known to be associated with deregulated angiogenesis.

One target identified in the cascade of events leading to angiogenesis is the Tie receptor family. The Tie-1 and Tie-2 receptors are single-transmembrane, tyrosine kinase receptors (Tie stands for tyrosine kinase receptors with immunoglobulin and EGF homology domains). Tie-2 is an endothelial cell specific receptor tyrosine kinase, which is involved in angiogenic processes, such as vessel branching, sprouting, remodeling, maturation and stability. Biological models suggest that the stimulation of Tie-2 by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial death, especially in the absence of growth/survival stimuli.

Recently, upregulation of Tie-2 expression has been found in the vascular synovial pannus of arthritic joints of humans, consistent with the role in inappropriate neovasculariation. This finding suggests that Tie-2 plays a role in the progression of rheumatoid arthritis. Point mutations producing constitutively activated forms of Tie-2 have been identified in association with human venous malformation disorders. Tie-2 inhibitors would, therefore, be useful in treating such disorders, as well as in other instances of improper neovasacularization. However, with the recent recognition of Ang3 and Ang4 as additional Tie-2 binding ligands, targeting a Tie-2 ligand-receptor interaction as an anti-angiogenic therapeutic approach is less favorable. Accordingly, a Tie-2 receptor kinase inhibition approach has become a strategy of choice.

Cancer and related oncological conditions are also caused by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation. Various kinase proteins have been identified, which play roles in the cell cycling cascade and in protein phosphorylation in particular.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 2, Aurora 1, and Aurora 3, respectively.

Aurora kinases appear to be viable targets for the treatment of cancer. Aurora kinases are overexpressed in various types of cancers, including colon, breast, lung, pancrease, prostate, bladder, head, neck, cervix, and ovarion cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Many classes of compounds have been proposed to generally or specifically inhibit kinase activity, including Aurora kinase. For example, WO 03/000660 describes substituted phenyl compounds, U.S. Pat. No. 6,143,764 describes substituted quinolines, WO 02/32872 describes substituted quinolines, WO 00/47212 describes substituted quinazoline derivatives, WO 04/039774 describes aza-quinazolinones for treating cancer via inhibition of Aurora kinase, WO 04/037814 describes indazolinones for treating cancer via inhibition of Aurora-2 kinase, WO 04/016612 describes 2,6,9-substituted purine derivatives for treating cancer via inhibition of Aurora kinase, WO 04/000833 describes tri- and tetra-substituted pyrimidine compounds useful for treating Aurora-mediated diseases and U.S. Pat. No. 6,919,338 and WO 03/055491 each describe substituted quinazoline derivatives as inhibitors of Aurora-2 kinase.

BRIEF DESCRIPTION OF THE INVENTION

The present invention provides a new class of compounds useful in treating oncological conditions and/or disease states related to kinase activity and, in particular, in treating active angiogenesis, cell-cycling disorders and related diseases, including cancer. In one embodiment of the invention, the compounds, including pharmaceutically acceptable salts thereof, are generally defined by Formula I

I

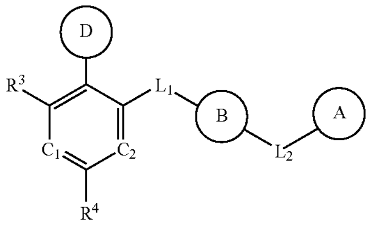

wherein A, B, $C^1$, $C^2$, D, $L^1$, $L^2$ and $R^{3-4}$ are defined herein.

In another embodiment, the invention further provides compounds of Formulas II and III, which are similar in structure to Formula I above.

The invention also provides processes for making compounds of Formulas I-III, as well as intermediates useful in such processes. In one embodiment, there is a method of making a compound of Formulas I-III, the method comprising the step of reacting compound of Formula A

A

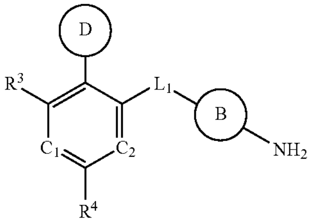

with a compound of Formula B

B

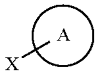

wherein A, B, $C^1$, $C^2$, D, $L^1$, $L^2$ and $R^{3-4}$ are defined herein and X is a halogen.

The compounds provided by the invention have kinase modulatory activity and, in particular, inhibitory activity, with respect to Tie-2 and/or Aurora kinase. To this end, the invention further provides the use of these compounds, as well as their pharmaceutically acceptable salts, in the preparation and/or manufacture of a medicament or pharmaceutical composition for therapeutic, prophylactic, acute or chronic treatment of an angiogenesis mediated disease state or a cell-cycling mediated disorder, including those described herein. Thus, the compounds described herein are useful as anti-cancer agents. More particularly, these compounds are useful in the manufacture of medicaments to attenuate or prevent disorders through inhibition of Tie-2 and/or Aurora kinase activity. For example, in one embodiment, the invention provides a pharmaceutical composition comprising a therapeutically-effective amount of a compound of Formula I, II or III in association with a least one pharmaceutically-acceptable carrier, adjuvant or diluent.

DETAILED DESCRIPTION OF THE INVENTION

In one embodiment of the invention, compounds, including stereoisomers, tautomers, solvates, pharmaceutically acceptable salts, derivatives and prodrugs thereof, useful for treating Tie-2 and/or Aurora kinase-mediated conditions, are defined by Formula I:

I

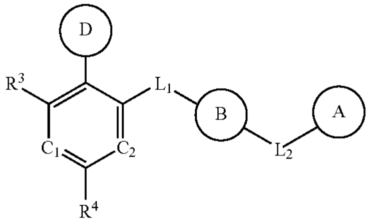

Wherein A is

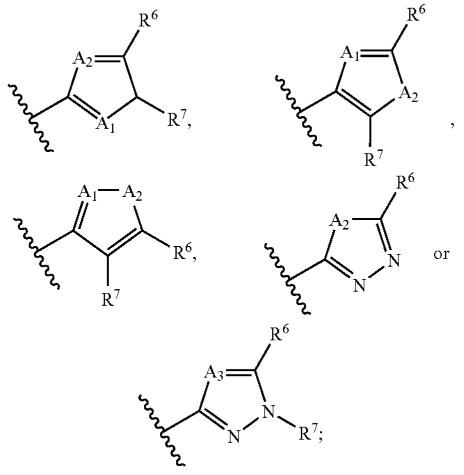

wherein each of $A^1$ and $A^3$ independently, is N or $CR^8$ and $A^2$ is $NR^9$, O or S;

B is a fully unsaturated 5-6 membered first monocyclic ring, said first ring (1) formed of carbon atoms optionally including 1-3 heteroatoms selected from O, N, or S, (2) optionally fused to a partially or fully saturated or fully unsaturated 5-6 membered second monocyclic ring formed of carbon atoms optionally including 1-3 heteroatoms selected from O, N, or S, and (3) wherein 0, 1, 2 or 3 atoms of each of said first and second ring is optionally substituted independently with 1-4 substituents of $R^5$;

$C^1$ is N or $CR^{10}$;

$C^2$ is N or CH;

D is

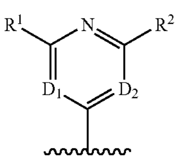

or

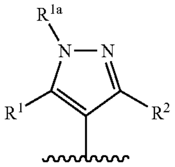

wherein $D^1$ is N or $CR^{11}$;

$D^2$ is N or $CR^{12}$;

$R^1$ is H, $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$, wherein n is 0, 1, 2, 3 or 4;

$R^{1a}$ is H, CN or $C_{1-10}$alkyl;

alternatively $R^1$ taken together with either of $R^{11}$ and $R^{1a}$ and the carbon or nitrogen atoms to which they are attached form a partially or fully unsaturated 5- or 6-membered ring of carbon atoms optionally including 1-3 heteroatoms selected from O, N and S, and the ring optionally substituted independently with 1-4 substituents of $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$; and $R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

$L^1$ is $NR^3$, O, S, C(O), S(O), $SO_2$ or $CR^3R^3$;

$L^2$ is $NR^3$, O, S, C(O), S(O), $SO_2$ or $CR^3R^3$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

each of $R^6$, $R^7$ and $R^8$, independently, is $R^{13}$, $R^{14}$ or $R^{15}$;

alternatively, $R^6$ and $R^7$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

$R^9$ is $R^{15}$;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$; and $R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

provided that (1) no more than one of $D^1$ and $D^2$ is N, and (2) each of $L^1$ and $L^2$ is, independently, bound to the first ring of B.

Accordingly, the above embodiment does not encompass triazine compounds, wherein both $D^1$ and $D^2$ are N, respectively. Triazine compounds (Formula III) of the present invention are described in another embodiment hereinbelow. In addition, the above embodiment includes only those compounds wherein both linkers $L^1$ and $L^2$ are bound to the first ring of B, and not compounds wherein one linker is attached to one ring of a fused bicyclic B ring while the second linker is attached to the second ring of B.

In another embodiment, the invention includes compounds wherein $C^1$ is N, in conjunction with any of the above or below embodiments.

In another embodiment, the invention includes compounds wherein $C^2$ is N, in conjunction with any of the above or below embodiments.

In another embodiment, the invention includes compounds wherein $C^1$ is $CR^{10}$, in conjunction with any of the above or below embodiments.

In another embodiment, the invention includes compounds wherein $C^2$ is H, in conjunction with any of the above or below embodiments.

In another embodiment, the invention includes compounds wherein D is

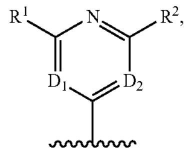

in conjunction with any of the above or below embodiments.

In another embodiment, the invention includes compounds wherein D is

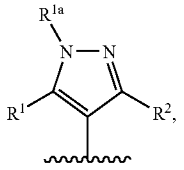

in conjunction with any of the above or below embodiments.

In another embodiment, the invention includes compounds wherein $R^{1a}$ is H, in conjunction with any of the above or below embodiments.

In another embodiment, the invention includes compounds wherein $R^{1a}$ a is CN or $C_{1-10}$alkyl, in conjunction with any of the above or below embodiments.

In another embodiment, the invention includes compounds wherein $D^1$ is N, in conjunction with any of the above or below embodiments.

In another embodiment, the invention includes compounds wherein $D^2$ is N, in conjunction with any of the above or below embodiments.

In another embodiment, the invention includes compounds wherein $D^1$ is $CR^{11}$, in conjunction with any of the above or below embodiments.

In another embodiment, the invention includes compounds wherein $D^2$ is $CR^{12}$, in conjunction with any of the above or below embodiments.

In another embodiment, the invention includes compounds wherein $D^2$ is N and $D^1$ is $CR^{11}$, in conjunction with any of the above or below embodiments.

In another embodiment, the invention includes compounds wherein $D^1$ is N and $D^2$ is $CR^{12}$, in conjunction with any of the above or below embodiments.

In another embodiment, the invention includes compounds wherein $C^1$ is $CR^{10}$, $C^2$ is N and $R^2$ is H, halo, $NO_2$, CN, $C_{1-10}$alkyl or $C_{1-10}$alkoxyl, in conjunction with any of the above or below embodiments.

In another embodiment, the invention includes compounds wherein $L^1$ is $NR^3$, in conjunction with any of the above or below embodiments.

In another embodiment, the invention includes compounds wherein $L^1$ is $NR^{15}$, in conjunction with any of the above or below embodiments.

In another embodiment, the invention includes compounds wherein $L^1$ is NH, in conjunction with any of the above or below embodiments.

In another embodiment, the invention includes compounds wherein $L^1$ is O, in conjunction with any of the above or below embodiments.

In another embodiment, the invention includes compounds wherein $L^1$ is S, in conjunction with any of the above or below embodiments.

In another embodiment, the invention includes compounds wherein $L^1$ is S(O), in conjunction with any of the above or below embodiments.

In another embodiment, the invention includes compounds wherein $L^1$ is $SO_2$, in conjunction with any of the above or below embodiments.

In another embodiment, the invention includes compounds wherein $L^1$ is $CR^3R^3$, in conjunction with any of the above or below embodiments.

In another embodiment, the invention includes compounds wherein $L^1$ is $CHR^{15}$, in conjunction with any of the above or below embodiments.

In another embodiment, the invention includes compounds wherein $L^1$ is $CH_2$, in conjunction with any of the above or below embodiments.

In another embodiment, the invention includes compounds wherein $L^2$ is $NR^3$, in conjunction with any of the above or below embodiments.

In another embodiment, the invention includes compounds wherein $L^2$ is $NR^{15}$, in conjunction with any of the above or below embodiments.

In another embodiment, the invention includes compounds wherein $L^2$ is NH, in conjunction with any of the above or below embodiments.

In another embodiment, the invention includes compounds wherein $L^2$ is O, in conjunction with any of the above or below embodiments.

In another embodiment, the invention includes compounds wherein $L^2$ is S, in conjunction with any of the above or below embodiments.

In another embodiment, the invention includes compounds wherein $L^2$ is S(O), in conjunction with any of the above or below embodiments.

In another embodiment, the invention includes compounds wherein $L^2$ is $SO_2$, in conjunction with any of the above or below embodiments.

In another embodiment, the invention includes compounds wherein $L^2$ is $CR^3R^3$, in conjunction with any of the above or below embodiments.

In another embodiment, the invention includes compounds wherein $L^2$ is $CHR^{15}$, in conjunction with any of the above or below embodiments.

In another embodiment, the invention includes compounds wherein $L^2$ is $CH_2$, in conjunction with any of the above or below embodiments.

In another embodiment, the invention includes compounds wherein $R^1$ is H, in conjunction with any of the above or below embodiments.

In another embodiment, the invention includes compounds wherein $R^1$ is $NR^{14}R^{15}$, in conjunction with any of the above or below embodiments.

In another embodiment, the invention includes compounds wherein $R^1$ is $NR^{15}R^{15}$, in conjunction with any of the above or below embodiments.

In another embodiment, the invention includes compounds wherein $R^1$ is $OR^{14}$, $SR^{14}$, $OR^{15}$, $SR^{15}$, or $(CHR^{15})_nR^{14}$ or $(CHR^{15})_nR^{15}$ wherein n is 0, 1, 2, 3 or 4, in conjunction with any of the above or below embodiments.

In another embodiment, the invention includes compounds wherein $R^1$ is $R^{15}$, in conjunction with any of the above or below embodiments.

In another embodiment, the invention includes compounds wherein each of $R^2$, $R^3$, $R^4$ and $R^5$, independently, is H, in conjunction with any of the above or below embodiments.

In another embodiment, the invention includes compounds wherein each of $R^2$, $R^3$, $R^4$ and $R^5$, independently, is $NR^{14}R^{15}$, in conjunction with any of the above or below embodiments.

In another embodiment, the invention includes compounds wherein each of $R^2$, $R^3$, $R^4$ and $R^5$, independently, is $NR^{15}R^{15}$, in conjunction with any of the above or below embodiments.

In another embodiment, the invention includes compounds wherein $R^2$ is $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$ or $NR^{15}S(O)_2R^{15}$, in conjunction with any of the above or below embodiments.

In another embodiment, the invention includes compounds wherein each of $R^2$, $R^3$, $R^4$ and $R^5$, independently, is $R^{15}$, in conjunction with any of the above or below embodiments.

In another embodiment, the invention includes compounds wherein $R^2$ is H, halo, $NO_2$, CN, $C_{1-10}$alkyl or $C_{1-10}$alkoxyl, in conjunction with any of the above or below embodiments.

In another embodiment, the invention includes compounds wherein each of $R^3$, $R^4$ and $R^5$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$ or $NR^{15}C(O)C(O)NR^{15}R^{15}$, in conjunction with any of the above or below embodiments.

In another embodiment, the invention includes compounds wherein either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$, in conjunction with any of the above or below embodiments.

In another embodiment, the invention includes compounds wherein $L^1$ is $NR^{15}$, O, $CHR^{15}$, S, C(O), S(O) or $SO_2$ and $R^2$ is H, halo, $NO_2$, CN, $C_{1-10}$alkyl or $C_{1-10}$alkoxyl, in conjunction with any of the above or below embodiments.

In another embodiment, the invention includes compounds wherein each of $L^1$ and $L^2$, independently, is $CHR^{15}$, $NR^{15}$, O, S, or C(O); $R^2$ is H, halo, $NO_2$, CN, $C_{1-10}$alkyl or $C_{1-10}$alkoxyl; each of $R^3$, $R^4$ and $R^9$, independently is H; and $C^1$ is $CR^{10}$, in conjunction with any of the above or below embodiments.

In another embodiment, the invention includes compounds wherein the first monocyclic ring of B is phenyl, pyridyl, pyrimidinyl, pyridazinyl, pyrazinyl, triazinyl, thiophenyl, furyl, pyrrolyl, pyrazolyl, imidazolyl, triazolyl, tetrazolyl, thiazolyl, thiadiazolyl, oxazolyl, oxadiazolyl, isoxazolyl, or isothiazolyl, in conjunction with any of the above or below embodiments.

In another embodiment, the invention includes compounds wherein the first monocyclic ring of B is a fully unsaturated 6-membered ring, and $L^1$ and $L^2$, together, are para to one another on said first monocyclic ring of B, in conjunction with any of the above or below embodiments.

In the immediately preceeding embodiment, the invention includes compounds wherein $R^6$ and $R^7$ taken together with the carbon atoms to which they are attached form a partially or fully unsaturated 5- or 6-membered ring of carbon atoms optionally including 1-3 nitrogen atoms, and the ring optionally substituted independently with 1-4 substituents of $R^{13}$, $R^{14}$ or $R^{15}$, in conjunction with any of the above or below embodiments.

In the immediately preceeding embodiment, the invention includes compounds wherein $R^6$ and $R^7$ taken together with the carbon atoms to which they are attached form a phenyl ring optionally including 1-3 nitrogen atoms, and the ring optionally substituted independently with 1-4 substituents of $R^{13}$, $R^{14}$ or $R^{15}$, in conjunction with any of the above or below embodiments.

In another embodiment, the invention includes compounds wherein A is

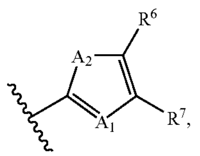

wherein $A^1$ is N and $A^2$ is NH, O or S, in conjunction with any of the above or below embodiments.

In the immediately preceeding embodiment, the invention includes compounds wherein $R^6$ and $R^7$ taken together with the carbon atoms to which they are attached form a phenyl ring optionally substituted independently with 1-4 substituents of $R^{15}$, in conjunction with any of the above or below embodiments.

In another embodiment, the invention includes compounds wherein A is

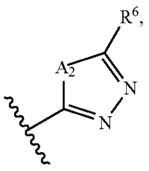

in conjunction with any of the above or below embodiments.

In another embodiment, the invention includes compounds wherein A is

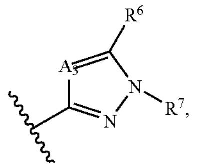

in conjunction with any of the above or below embodiments.

In another embodiment, the invention includes compounds wherein A is

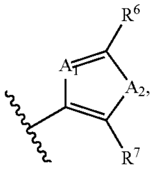

in conjunction with any of the above or below embodiments.

In another embodiment, the invention includes compounds wherein A is

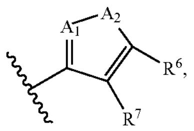

in conjunction with any of the above or below embodiments.

In the previous three embodiments, the invention includes compounds wherein $A^1$ is N, in conjunction with any of the above or below embodiments.

In the previous three embodiments, the invention includes compounds wherein $A^1$ is $CR^8$, in conjunction with any of the above or below embodiments.

In the previous three embodiments, the invention includes compounds wherein $A^3$ is N, in conjunction with any of the above or below embodiments.

In the previous three embodiments, the invention includes compounds wherein $A^3$ is $CR^8$, in conjunction with any of the above or below embodiments.

In the previous three embodiments, the invention includes compounds wherein $A^2$ is $NR^9$, in conjunction with any of the above or below embodiments.

In the previous three embodiments, the invention includes compounds wherein $A^2$ is NH, in conjunction with any of the above or below embodiments.

In the previous three embodiments, the invention includes compounds wherein $A^2$ is N—$C_{1-10}$-alkyl, in conjunction with any of the above or below embodiments.

In the previous three embodiments, the invention includes compounds wherein $A^2$ is O, in conjunction with any of the above or below embodiments.

In the previous three embodiments, the invention includes compounds wherein $A^2$ is S, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- and heteroaryl-alkyl-amino- as $R^1$, in conjunction with any of the above or below embodiments.

In another embodiment, the compounds of Formula I include $R^1$ taken together with $R^{11}$ to form a partially or fully unsaturated 5- or 6-membered ring of carbon atoms optionally including 1-3 heteroatoms selected from O, N and S, and the ring optionally substituted independently with 1-4 substituents of $R^{15}$, halo, haloalkyl, oxo, $NO_2$, CN, $SR^{15}$, $OR^{15}$, $OC(O)R^{15}$, $COOR^{15}$, $C(O)R^{15}$, $C(O)NR^{15}R^{15}$, $NR^{15}R^{15}$ or $NR^{14}R^{15}$, in conjunction with any of the above or below embodiments.

In another embodiment, the compounds of Formula I include H, halo, haloalkyl, oxo, $NO_2$, CN, $SR^{15}$, $OR^{15}$, $NR^{15}R^{15}$, $NR^{14}R^{15}$, $C(O)R^{15}$, $COOR^{15}$, $OC(O)R^{15}$, $C(O)C(O)R^{15}$, $C(O)NR^{15}R^{15}$, $C(O)NR^{14}R^{15}$, $NR^{15}C(O)R^{15}$, $NR^{15}C(O)R^{14}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{15}$, $S(O)_2NR^{15}R^{15}$, $NR^{15}S(O)_2NR^{15}R^{15}$, $NR^{15}S(O)_2R^{15}$, $NR^{15}S(O)_2R^{14}$, $NR^{15}C(O)C(O)NR^{15}R^{15}$, $NR^{15}C(O)C(O)NR^{14}R^{15}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{15}$, as $R^2$, in conjunction with any of the above or below embodiments.

In another embodiment, the compounds of Formula I include H, halo, haloalkyl, $NO_2$, CN, $SR^{15}$, $OR^{15}$, $NR^{15}R^{15}$, $C_{1-10}$alkyl, $C_{1-10}$alkenyl or $C_{1-10}$alkynyl, wherein the $C_{1-10}$alkyl, $C_{1-10}$alkenyl and $C_{1-10}$alkynyl, is optionally substituted with one or more substituents of $R^{15}$, as $R^2$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- and heteroaryl-alkyl-amino- as $R^2$, in conjunction with any of the above or below embodiments.

In another embodiment, the compounds of Formula I include $R^1$ taken together with $R^{1a}$ to form a partially or fully unsaturated 5- or 6-membered ring of carbon atoms optionally including 1-3 heteroatoms selected from O, N and S, and the ring optionally substituted independently with 1-4 substituents of $R^{15}$, halo, haloalkyl, oxo, $NO_2$, CN, $SR^{15}$, $OR^{15}$, $OC(O)R^{15}$, $COOR^{15}$, $C(O)R^{15}$, $C(O)NR^{15}R^{15}$, $NR^{15}R^{15}$ or $NR^{14}R^{15}$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- and heteroaryl-alkyl-amino- as $R^3$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl; heteroaryl-amino-, aryl-alkyl-amino-, heterocyclyl-alkyl-amino- and heteroaryl-alkyl-amino- as $R^4$, in conjunction with any of the above or below embodiments.

In another embodiment, the compounds of Formula I include H, halo, haloalkyl, oxo, $NO_2$, CN, $SR^{15}$, $OR^{15}$, $NR^{15}R^{15}$, $NR^{14}R^{15}$, $C(O)R^{15}$, $COOR^{15}$, $OC(O)R^{15}$, $C(O)C(O)R^{15}$, $C(O)NR^{15}R^{15}$, $C(O)NR^{14}R^{15}$, $NR^{15}C(O)R^{15}$, $NR^{15}C(O)R^{14}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{15}$, $S(O)_2NR^{15}R^{15}$, $NR^{15}S(O)_2NR^{15}R^{15}$, $NR^{15}S(O)_2R^{15}$, $NR^{15}S(O)_2R^{14}$, $NR^{15}C(O)C(O)NR^{15}R^{15}$, $NR^{15}C(O)C(O)NR^{14}R^{15}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{15}$, as $R^5$, in conjunction with any of the above or below embodiments.

In another embodiment, the compounds of Formula I include H, Cl, Br, F, I, $CF_3$, $CF_2CF_3$, $NO_2$, CN, acetyl, oxo, haloalkyl, haloalkoxyl, CN, OH, SH, $NO_2$, $NH_2$, acetyl, $C_{1-10}$-alkylamino-, benzyl or phenyl as $R^5$, in conjunction with any of the above or below embodiments.

In another embodiment, the compounds of Formula I include H, halo, haloalkyl, oxo, $NO_2$, CN, $SR^{15}$, $OR^{15}$, $NR^{15}R^{15}$, $NR^{14}R^{15}$, $C(O)R^{15}$, $COOR^{15}$, $OC(O)R^{15}$, C(O)C (O)$R^{15}$, C(O)$NR^{15}R^{15}$, C(O)$NR^{14}R^{15}$, $NR^{15}$C(O)$R^{15}$, $NR^{15}$C(O)$R^{14}$, $NR^{15}$C(O)$NR^{15}R^{15}$, $NR^{15}$C(O)C(O)$R^{15}$, $NR^{15}$($COOR^{15}$), OC(O)$NR^{15}R^{15}$, $S(O)_2R^{15}$, $S(O)_2NR^{15}R^{15}$, $NR^{15}S(O)_2NR^{15}R^{15}$, $NR^{15}S(O)_2R^{15}$, $NR^{15}S(O)_2R^{14}$, $NR^{15}$C(O)C(O)$NR^{15}R^{15}$, $NR^{15}$C(O)C(O)$NR^{14}R^{15}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{15}$, as $R^6$, in conjunction with any of the above or below embodiments.

In another embodiment, the compounds of Formula I include H, Cl, Br, F, I, $CF_3$, $CF_2CF_3$, $NO_2$, CN, acetyl, oxo, haloalkyl, haloalkoxyl, CN, OH, SH, $NO_2$, $NH_2$, acetyl, $C_{1-10}$-alkylamino-, benzyl or phenyl as $R^6$, in conjunction with any of the above or below embodiments.

In another embodiment, the compounds of Formula I include H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl as $R^7$, in conjunction with any of the above or below embodiments.

In another embodiment, the compounds of Formula I include H, halo, haloalkyl, $C_{1-10}$-alkyl, $C_{1-10}$-alkylamino-, $C_{1-10}$-dialkylamino- or $C_{1-10}$-alkoxyl as $R^7$, in conjunction with any of the above or below embodiments.

In another embodiment, the compounds of Formula I include H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{4-10}$-alkylamino-, $C_{1-10}$-alkylamino-, $C_{1-10}$-alkoxyl or $C_{1-10}$-thioalkoxyl as $R^8$, in conjunction with any of the above or below embodiments.

In another embodiment, the compounds of Formula I include H, halo, haloalkyl, $C_{1-10}$-alkyl, $C_{1-10}$-alkylamino-, $C_{1-10}$-dialkylamino- or $C_{1-10}$-alkoxyl as $R^8$, in conjunction with any of the above or below embodiments.

In another embodiment, the compounds of Formula I include H, halo, haloalkyl, $NO_2$, CN, $SR^{15}$, $OR^{15}$, $NR^{15}R^{15}$ or C(O)$R^{15}$ as $R^9$, in conjunction with any of the above or below embodiments.

In another embodiment, the compounds of Formula I include H as $R^{10}$, in conjunction with any of the above or below embodiments.

In another embodiment, the compounds of Formula I include H, halo, haloalkyl, $NO_2$, CN, $SR^{15}$, $OR^{15}$, $NR^{15}R^{15}$, $NR^{14}R^{15}$, C(O)$R^{15}$, $COOR^{15}$, OC(O)$R^{15}$, C(O)C(O)$R^{15}$, C(O)$NR^{15}R^{15}$, $NR^{15}$C(O)$R^{15}$, $NR^{15}$($COOR^{15}$), OC(O)$NR^{15}R^{15}$, $NR^{15}$C(O)$NR^{15}R^{15}$, C(S)$R^{15}$, C(S)$NR^{15}R^{15}$, $NR^{15}$C(S)$R^{15}$, $NR^{15}$C(S)$NR^{15}R^{15}$, $S(O)_2R^{13}$, $S(O)_2NR^{13}R^{13}$, $S(O)_2NR^{15}R^{15}$, $NR^{15}S(O)_2NR^{15}R^{13}$ or $NR^{15}S(O)_2R^{15}$ as $R^{10}$, in conjunction with any of the above or below embodiments.

In another embodiment, the compounds of Formula I include H, halo, haloalkyl, $NO_2$, CN, $SR^{15}$, $OR^{15}$, $NR^{15}R^{15}$, $NR^{14}R^{15}$, C(O)$R^{15}$, $COOR^{15}$, OC(O)$R^{15}$, C(O)C(O)$R^{15}$, C(O)$NR^{15}R^{15}$, $NR^{15}$C(O)$R^{15}$, $NR^{15}$($COOR^{15}$), OC(O)$NR^{15}R^{15}$, $NR^{15}$C(O)$NR^{15}R^{15}$, C(S)$R^{15}$, C(S)$NR^{15}R^{15}$, $NR^{15}$C(S)$R^{15}$, $NR^{15}$C(S)$NR^{15}R^{15}$, $S(O)_2R^{13}$, $S(O)_2NR^{13}R^{13}$, $S(O)_2NR^{15}R^{15}$, $NR^{15}S(O)_2NR^{15}R^{13}$ or $NR^{15}S(O)_2R^{15}$ as $R^{12}$, in conjunction with any of the above or below embodiments.

In another embodiment, the compounds of Formula I include cyclopropyl, cyclobutyl, cyclopentyl, cyclohexyl, tetrahydrofuranyl, tetrahydropyrrolyl, pyranyl, phenyl, naphthyl, furanyl, pyrrolyl, thiophenyl, indolyl, imidazolyl, pyrazolyl, thiazolyl, isothiazolyl, oxazolyl, isoxazolyl, thiadiazolyl, triazolyl, tetrazolyl, benzofuranyl, benzothiophenyl, indolinyl, phthalazinyl, benzimidazolyl, benzopyrazolyl, benzoxazolyl, benzothiozolyl, benzisoxazolyl, piperidinyl, piperazinyl, morpholinyl, each of which is optionally independently substituted with 1-3 substituents of $R^{15}$, as $R^{14}$, in conjunction with any of the above or below embodiments.

In yet another embodiment of the invention, compounds useful for treating angiogenesis and cancer are generally defined by Formula II:

II

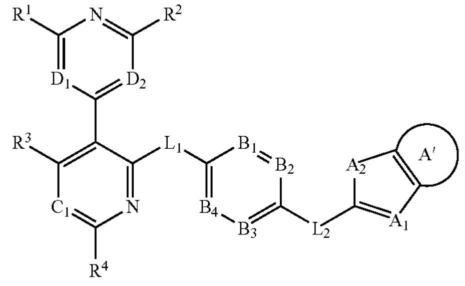

wherein $A^1$ is N or $CR^8$;

$A^2$ is $NR^9$, O or S;

A' is phenyl, pyridine, pyrimidine or pyridazine, each of which is optionally substituted independently with 1-3 substituents of $R^{13}$, $R^{14}$ or $R^{15}$;

each of $B^1$, $B^2$, $B^3$ and $B^4$, independently, is N or $CR^5$, provided that no more than two of $B^1$, $B^2$, $B^3$ and $B^4$ is N;

alternatively, each of $B^1$ and $B^2$, independently, is $CR^5$, wherein both $R^5$ groups taken together with the carbon atoms to which they are attached form a 5- or 6-membered ring of carbon atoms, said ring optionally including 1-4 heteroatoms selected from N, O or S, and optionally substituted with 1-3 substituents of $R^{13}$, $R^{14}$ or $R^{15}$;

$C^1$ is N or $CR^{10}$;

$D^1$ is N or $CR^{11}$;

$D^2$ is N or $CR^{12}$;

$L^1$ is $NR^3$, O, S or $CR^3R^3$;

$L^2$ is $NR^3$, O, S or $CR^3R^3$;

$R^1$ is $OR^{14}$, $SR^{14}$, $OR^{15}$, $SR^{15}$, $NR^{14}R^{15}$, $NR^{15}R^{15}$, $(CHR^{15})_nR^{14}(CHR^{15})_nR^{15}$ or $R^{15}$, wherein n is 0, 1, 2, 3 or 4;

alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-4 substituents of $R^{15}$, $SR^{14}$, $OR^{14}$, $SR^{15}$, $OR^{15}$, OC(O)$R^{15}$, $COOR^{15}$, C(O)$R^{15}$, C(O)$NR^{15}R^{15}$, $NR^{14}R^{15}$ or $NR^{15}R^{15}$;

$R^2$ is $SR^{14}$, $OR^{14}$, $SR^{15}$, $OR^{15}$, $NR^{14}R^{15}$, $NR^{15}R^{15}$, C(O)$R^{14}$, C(O)$R^{15}$, $COOR^{15}$, OC(O)$R^{15}$, C(O)C(O)$R^{15}$, C(O)$NR^{14}R^{15}$, C(O)$NR^{15}R^{15}$, $NR^{15}$C(O)$R^{14}$, $NR^{15}$C(O)$R^{15}$, $NR^{15}$C(O)$NR^{14}R^{15}$, $NR^{15}$C(O)$NR^{15}R^{15}$, $NR^{15}$C(O)C(O)$R^{15}$, $NR^{15}$($COOR^{15}$), OC(O)$NR^{15}R^{15}$, $S(O)_2R^{14}$, $S(O)_2R^{15}$, $S(O)_2NR^{14}R^{15}$, $S(O)_2NR^{15}R^{15}$, $NR^{15}$, $S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

each of $R^3$ and $R^4$, independently, is $SR^{14}$, $OR^{14}$, $SR^{15}$, $OR^{15}$, $NR^{14}R^{15}$, $NR^{15}R^{15}$, C(O)$R^{14}$, C(O)$R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each $R^{15}$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^8$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^9$ is H, halo, haloalkyl, haloalkoxyl, oxo, CN, OH, SH, $NO_2$, $NH_2$, acetyl, $C_{1-10}$-alkyl, $C_{1-10}$-alkoxyl, $C_{2-10}$-alkenyl, $C_{2-10}$-alkynyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{1-10}$-alkoxyl, $C_{2-10}$-alkenyl, $C_{2-10}$-alkynyl, and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$; and $R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

provided that no more than one of $D^1$ and $D^2$ is N.

In another embodiment, the invention includes compounds of Formula II, wherein:

$A^1$ is N;

$A^2$ is $NR^9$, O or S;

each of $B^1$, $B^2$, $B^3$ and $B^4$, independently, is $CR^5$;

$C^1$ is $CR^{10}$;

$D^1$ is N or $CR^{11}$;

$D^2$ is N or $CR^{12}$;

$L^1$ is NH, O or S;

$L^2$ is NH, O or S;

$R^1$ is H, halo, haloalkyl, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl, $NHR^{14}$, $NHR^{15}$, $OR^{15}$, $SR^{15}$ or $CH_2R^{15}$;

$R^2$ is H, halo, $NO_2$, CN, $C_{1-10}$alkyl or $C_{1-10}$alkoxyl;

each of $R^3$ and $R^4$, independently, is $SR^{15}$, $OR^{15}$, $NR^{14}R^{15}$, $NR^{15}R^{15}$, $C(O)R^{14}$, $C(O)R^{15}$ or $R^{15}$;

each $R^5$ is, independently, is $SR^{15}$, $OR^{15}$, $NR^{15}R^{15}$, $C(O)R^{15}$, $C(O)NR^{15}R^{15}$, $NR^{15}C(O)R^{15}$, $NR^{15}C(O)NR^{15}R^{15}$, $NR^{15}(COOR^{15})$, $S(O)_2R^{15}$, $S(O)_2NR^{15}R^{15}$, $NR^{15}S(O)_2NR^{15}R^{15}$, $NR^{15}S(O)_2R^{15}$, $NR^{15}C(O)C(O)NR^{14}R^{15}$ or $R^{15}$; and $R^8$ is $SR^{15}$, $OR^{15}$, $NR^{15}R^{15}$, $C(O)R^{15}$ or $R^{15}$;

$R^9$ is H, CN, acetyl or $C_{1-10}$-alkyl; and each of $R^{10}$, $R^{11}$ and $R^{12}$, independently, is $SR^{15}$, $OR^{15}$, $NR^{15}R^{15}$, $C(O)R^{14}$, $C(O)R^{15}$ or $R^{15}$, in conjunction with any of the above or below embodiments.

In another embodiment, the invention includes compounds of Formula II, wherein:

$R^1$ is $NR^{14}R^{15}$, $NR^{15}R^{15}$, $(CHR^{15})_nR^{14}$, $(CHR^{15})_nR^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-4 substituents of $R^{15}$;

$R^2$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

each of $R^3$ and $R^4$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

each $R^5$ is, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;

$R^8$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;

$R^9$ is H or $C_{1-10}$-alkyl; and each of $R^{10}$, $R^{11}$ and $R^{12}$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine, in conjunction with any of the above or below embodiments.

The embodiments for various of the elements described herein above with respect to compounds of Formula I also apply to compounds of Formula II, where appropriate, as will be appreciated by those skilled in the art.

In another embodiment, the invention includes compounds of Formula III

III

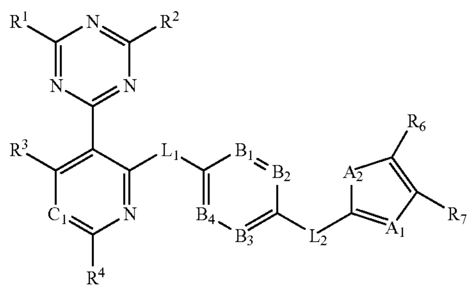

wherein $A^1$ is N or $CR^8$;

$A^2$ is $NR^9$, O or S;

each of $B^1$, $B^2$, $B^3$ and $B^4$, independently, is N or $CR^5$, provided that no more than two of $B^1$, $B^2$, $B^3$ and $B^4$ is N;

$C^1$ is N or $CR^{10}$;

$L^1$ is O, S, C(O), S(O), $SO_2$ or $CR^3R^3$;

$L^2$ is $NR^3$, O, S or $CR^3R^3$;

$R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$;

$R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

each of $R^6$, $R^7$ and $R^8$, independently, is $R^{13}$, $R^{14}$ or $R^{15}$;

alternatively, $R^6$ and $R^7$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

$R^9$ is $R^{15}$;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$;

$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3 or 4.

The embodiments for various of the elements described herein above with respect to compounds of Formula I also apply to compounds of Formula III, where appropriate, as will be appreciated by those skilled in the art.

In yet another embodiment, Formulas I, II and III include the exemplary compounds and derivatives, prodrugs, solvates, tautomers and pharmaceutically acceptable salt forms thereof, intermediates related thereto, which are described in the Examples herein.

DEFINITIONS

The following definitions should further assist in understanding the invention and its scope as described herein.

The terms "agonist" and "agonistic" when used herein refer to or describe a molecule which is capable of, directly or indirectly, substantially inducing, promoting or enhancing biological activity of a biological molecule, such as an enzyme or receptor, including Tie-2 and Aurora kinase.

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction and/or flow properties to improve blood perfusion of tissue.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Tie-2 and/or Aurora kinase in the mammal.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), ester of a compound of this invention, or any other compound which upon administration to a patient is capable of providing (directly or indirectly) a compound of this invention, or a metabolite or residue thereof, characterized by the ability to treat a condition related to the activity of one or more kinase enzymes.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The terms "ring" and "ring system" refer to a one or more rings, typically fused together where more than one ring, comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "non-aromatic" ring or ring system refers to the fact that at least one, but not necessarily all, rings in a bicyclic or tricyclic ring system is not fully unsaturated.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated. The term "alkylenyl" embraces bridging divalent alkyl radicals such as methylenyl and ethylenyl.

The term "alkenyl", alone or in combination, embraces linear or branched radicals having at least one carbon-carbon double bond of two or more carbon atoms. Examples of alkenyl radicals include, without limitation, ethenyl, propenyl, allyl, propenyl, butenyl and 4-methylbutenyl. The terms "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of such radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine, chlorine, bromine or iodine atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "hydroxyalkyl", alone or in combination, embraces linear or branched alkyl radicals having one or more carbon atoms any one of which may be substituted with one or more hydroxyl radicals. Examples of such radicals include hydroxymethyl, hydroxyethyl, hydroxypropyl, hydroxybutyl and hydroxyhexyl.

The term "alkoxy", alone or in combination, embraces linear or branched oxy-containing radicals each having alkyl portions of alpha to beta number of carbon atoms. For example, a $C_{1-10}$alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "partially or fully saturated" as used herein, refers to a moiety, linear, branched or cyclic in nature, having no atom-atom double or triple bonds, and one or more atom-atom double or triple bonds, arranged such that wherein the structure is cyclic, the ring structure is not aromatic, as appreciated by those skilled in the art.

The term "fully unsaturated" as used herein, refers to a moiety having double or triple bonds, arranged in a manner such that the structure is aromatic, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 to 3 substituents such as alkyl, hydroxyl, halo, haloalkyl, nitro, cyano, alkoxy and alkylamino, and the like. Phenyl substituted with —O—$CH_2$—O— forms an aryl benzodioxolyl substituent. Aryl as used herein, implies a fully unsaturated ring.

The term "heterocycles" or "heterocyclic radicals", alone or in combination, embraces saturated, partially saturated and unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 to 3 substituents such as hydroxyl, Boc, halo, haloalkyl, cyano, alkyl, ralkyl, oxo, alkoxy, amino and alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also referred to herein as "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals $—SO_2—$.

The term "carbonyl", whether used alone or with other terms, such as "aminocarbonyl", denotes —(C═O)—.

The term "aminocarbonyl" denotes an amide group of the formula $—C(═O)NH_2$.

The term "aralkyl" embraces aryl-substituted alkyl radicals. Examples of such radicals include benzyl, diphenylmethyl and phenylethyl. The aryl in said aralkyl may be additionally substituted with halo, alkyl, alkoxy, halkoalkyl and haloalkoxy.

The term "aminoalkyl" and "diaminoalkyl" embraces "N-alkylamino" and "N,N-dialkylamino", respectively, where amino groups are independently substituted with one alkyl radical and with two alkyl radicals, respectively. Suitable alkylamino radicals may be mono or dialkylamino such as N-methylamino, N-ethylamino, N,N-dimethylamino, N,N-diethylamino and the like.

The term "$C_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidyl-methyl-amino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "comprising" is meant to be open ended, including the indicated component(s) but not excluding other elements.

The terms "Formula I", "Formula II" and "Formula III" include any sub formulas.

The present invention comprises processes for the preparation of a compound of Formulas I and II.

Also included in the family of compounds of Formulas I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-III may be prepared from an inorganic acid or from an organic acid. Examples of such inorganic acids are hydrochloric, hydrobromic, hydroiodic, nitric, carbonic, sulfuric and phosphoric acid. Suitable exemplary organic acids include, without limitation, aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-III include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I-III. When a basic group and an acid group are present in the same molecule, a compound of Formulas I-III may also form internal salts.

General Synthetic Procedures

The compounds of the invention can be synthesized according to the following procedures of Schemes 1-9, wherein the substituents are as defined for Formulas I-III, above, except where further noted. The synthetic methods described below are merely exemplary, and the compounds of the invention may be synthesized by alternate routes as appreciated by persons of ordinary skill in the art.

The following list of abbreviations used throughout the specification represent the following:

| | |
|---|---|
| BSA | bovine serum albumin |
| $Cs_2CO_3$ | cesium carbonate |
| $CHCl_3$ | chloroform |
| DCM, MC | dichloromethane, methylene chloride |
| DIBAL | diisobutylaluminum hydride |
| DIEA, $(iPr)_2Net$ | diisopropylethylamine |
| DME | dimethoxyethane |
| DMF | dimethylformamide |
| DMAP | 4-dimethylaminopyridine |
| DMSO | dimethylsulfoxide |
| $Et_2O$ | diethyl ether |
| EtOAc | ethyl acetate |
| FBS | fetal bovine serum |
| G, gm | gram |
| h, hr | hour |
| HBr | hydrobromic acid |
| HCl | hydrochloric acid |
| HOBt | 1-hydroxybenzotriazole hydrate |
| $H_2$ | hydrogen |
| $H_2O_2$ | hydrogen peroxide |
| HPLC | high pressure liquid chromatography |
| IPA, IpOH | isopropyl alcohol |
| $K_2CO_3$ | potassium carbonate |
| $MgSO_4$ | magnesium sulfate |
| MeOH | methanol |
| $N_2$ | nitrogen |
| $NaHCO_3$ | sodium bicarbonate |
| NaOH | sodium hydroxide |
| NaH | sodium hydride |
| $Na_2SO_4$ | sodium sulfate |
| $NH_4Cl$ | ammonium chloride |
| $NH_4OH$ | ammonium chloride |
| PBS | phospate buffered saline |
| Pd/C | palladium on carbon |
| $Pd(PPh_3)_4$ | palladium(0)triphenylphosphine tetrakis |
| $Pd(OAc)_2$ | palladium acetate |
| RT | room temperature |
| TEA, $Et_3N$ | triethylamine |
| TFA | trifluoroacetic acid |
| THF | tetrahydrofuran |

Scheme 1

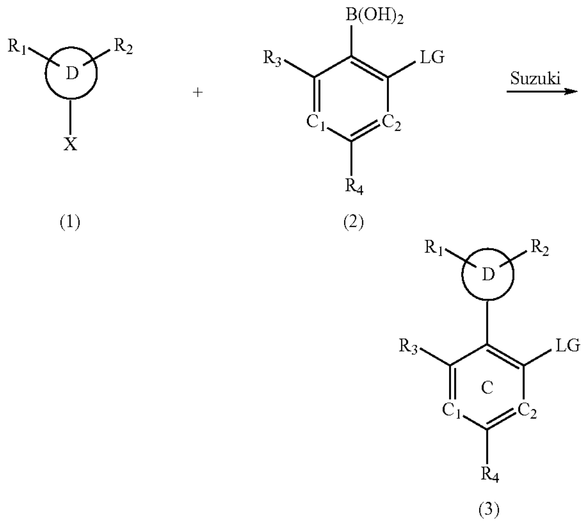

The biaryl ring system (3), including substituted or unsubstituted pyridyl-pyridines (where ring C and D are both pyridines), pyridyl-pyrimidines (where one of rings C and D is a pyridine and the other is a pyrimidine), pyridyl triazines (where D is a triazine), pyrimidyl-pyrimidines and pyrimidyl-triazines (where ring D is a triazine) and generally referred to herein as the C-D ring portion of the compounds of Formulas I-III, can be prepared according to the method generally described in Scheme 1. As shown, Suzuki coupling methodology utilizing an aryl halide (1) where X is a halide such as iodide, bromide or chloride, and an aryl borinate (2) in the presence of palladium, such as $Pd(PPh_3)_4$, and a weak base, such as a $Na_2CO_3$, $K_2CO_3$ or $NaHCO_3$ in a polar solvent such as DME can be used to synthesize compound (3). LG is a known leaving group, such as F or Cl. Similarly, other known aryl coupling methods, such as use of stannanes, zincates and copper coupling techniques are also suitable to prepare compound (3).

In a similar manner, phenyl-pyridines, phenyl-pyrimidines and phenyl-triazine C-D rings of the compounds of Formulas I-III, can also be prepared according to the Suzuki or other metallation chemistry methods, wherein the aryl borinate (2) is a desirably substituted phenyl borinate, as described in Scheme 1.

Alternatively, amino-substituted pyridyl pyrimidines C-D ring systems (8) can be prepared according to the method shown in Scheme 2.

dine acetate. Desirable amino-$R^1$ groups can be installed at the 3 position of the 4,6-pyrimidine D-ring by simply treating compound (7) with a primary or secondary amine, having the desired substitution, with heat under conditions milder than those required to displace the pyridyl chloride of compound (6). Further, compound (6) can be treated with p-toluene sulfonyl chloride, or other similar activating reagents to render the pyrimidine hydroxyl group into a suitable leaving group (LG) for displacement with a desired, sufficiently reactive nucleophile, including amines, sulfur, and oxygen nucleophiles. Also, compound (6) may be treated with a base sufficiently strong to deprotonate the hydroxyl proton in order to alkylate the hydroxyl group, thereby forming an ether, alkoxy moiety, and the like. Further, compound (6) can be converted to the corresponding thiol utilizing reactions and techniques known in the art. This thiol (not shown 0 may then be converted to corresponding thio-linked $R^1$ groups. In addition, compound (7) can be treated with ammonia to give the amino adduct, which then can be alkylated, acylated, or otherwise substituted with a desired group. Such methods are known to those skilled in the art, and are described in Jerry Scheme 2

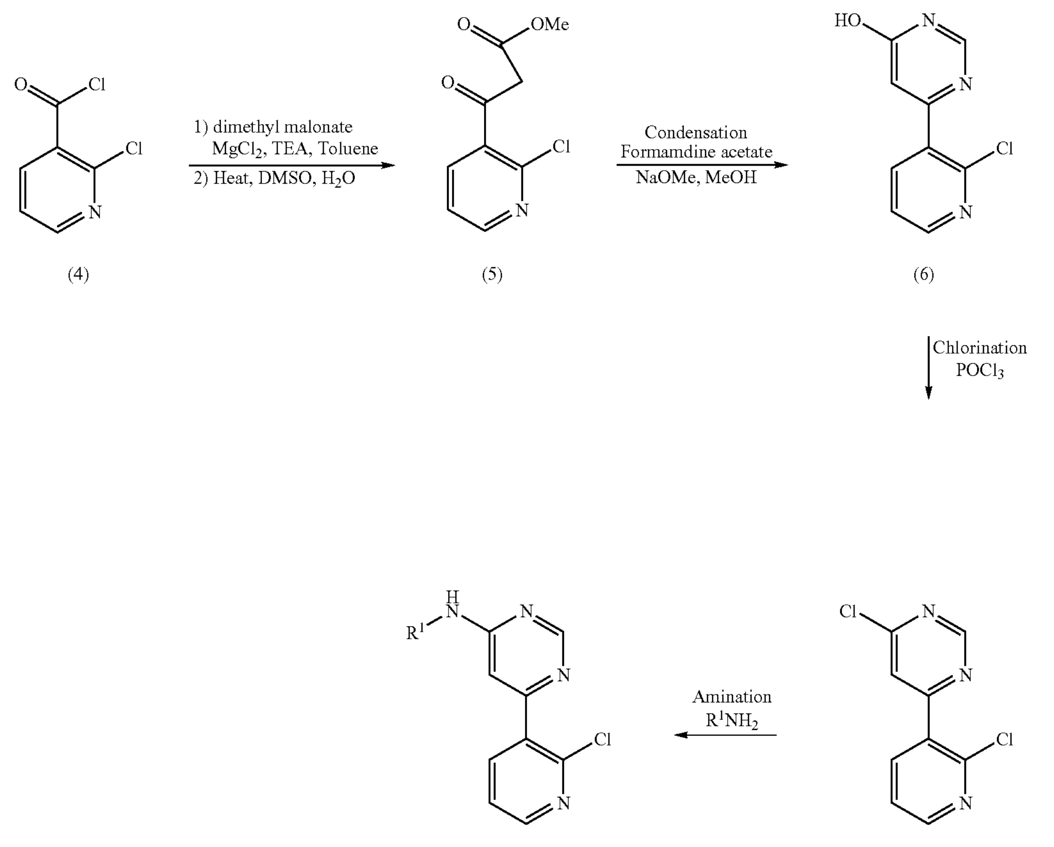

(4) (5) (6)

(8) (7)

Chloro-nicotinic acid chlorides (4) can be treated with dimethylmalonate in the presence of a suitable base and MgCl to form intermediate (5). Compound (5) can be cyclized to form the hydroxyl-substituted pyrimidyl-pyridine compound (6), in the presence of suitable base and formami- March's Advanced Organic Chemistry, $4^{th}$ edition (1992), which disclosure is hereby incorporated by reference in its entirety.

The 2,4-regioisomer of the above pyridyl-pyrimidines can also be made using the following Scheme 3.

Scheme 3

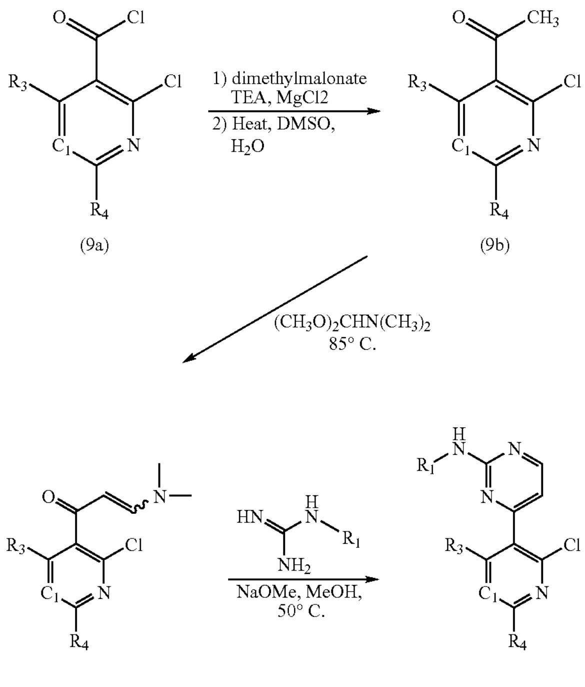

(9a) (9b) (9c) (10)

Compound (10) can be made by treating the acid chloride of compound (9a) (ring C) and converting it to the corresponding methyl ketone (9b) followed by treatment with dimethyl formamide dimethylacetal to obtain the corresponding enaminone (9c). Then substituted guanidine HCl can be treated with a suitable base, such as sodium methoxide, for a time period prior to exposing the guanidine mixture to the enaminone (9c) to form the pyridyl pyrimidine (10). This method allows desired $R^1$ groups to be installed prior to ring closure. Care must be taken to restrict the $R^1$ groups in this method to those, which would not interfere with or react during formation of intermediates 9a—9c and also ring closure to form compound (10), as appreciated by persons of ordinary skill in the art.

Alternatively, compound (9c) can be treated with guanidine HCl in the presence of NaOH in isopropanol to afford the corresponding 3-amino-pyrimidine D ring (not shown, where $R^1$ is $NH_2$). The $R^1$ position of this intermediated can be modified using reductive alkylation methods with corresponding aldehydes, acylation methods, and other groups, by methods appreciated by persons of ordinary skill in the art, to install the desired groups at this position on the D ring of compounds of Formulas I-III. Alternatively, the 3-aminopyrimidine may be converted to 3-fluoropyrimidine with use of t-butyl nitrate and HF pyridine, and the fluoride then displaced with a desired $R^1$ group such as $NH_2R$, OR and SR. This latter technique may also be used to convert amino-triazines to the corresponding fluoro-triazines.

Similarly, pyridyl-triazines C-D biaryl ring systems can be made using the method of Scheme 4.

Scheme 4

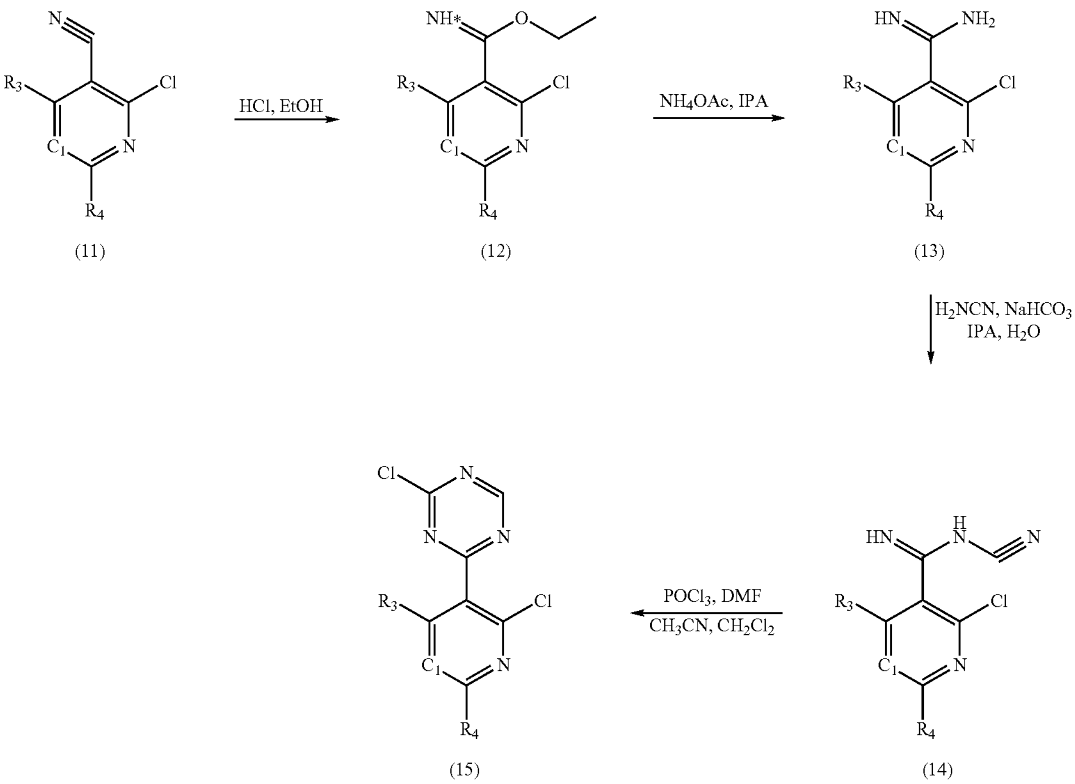

(11) (12) (13) (14) (15)

In a manner similar to the method illustrated and described in Scheme 2, desirable amino-$R^1$ groups can be installed at the 3 position of a triazine D ring by treating compound (15) with a primary or secondary amine, having the desired substitution, with heat under conditions less strenuous than required to displace the pyridyl chloride of compound (15).

The C-D ring portion of the compounds of Formulas I-III can be attached to the B ring of compound (17 or 17a—see scheme 5 below) by a number of conventional methods known in the art, as disclosed in March. Suitable methods are illustrated in Schemes 5 and 6 below.

Scheme 5

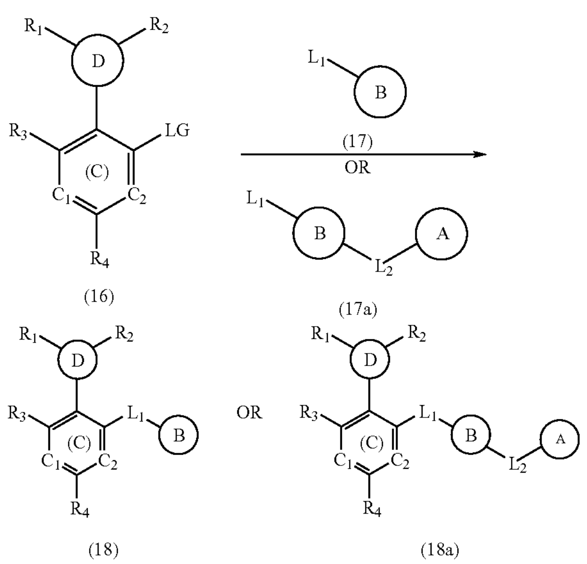

(16) (17a) (18) OR (18a)

As shown in Scheme 5, compound (18 or 18a) comprising biaryl ethers and thiols (where $L^1$=O and S, respectively) can be prepared by reacting compound (16) (where LG is a leaving group, such as a halide, like a chlorine or bromine) with a nucleophilic phenyl compound (17) wherein $L^1$ is a suitable nucleophile, such as OH or SH (Scheme 5), or NHR or $NH_2$ (Scheme 6) or carbon nucleophile, sufficient to displace the chloride from ring C of compound (16). For example, phenols ($L^1$=O) and thiols ($L^1$=S) can be coupled with activated aryl chlorides to form the biaryl ethers and thiols (compound 18) using weak bases such as TEA, or inorganic bases such as $Cs_2CO_3$, in DMSO at elevated temperatures, such as ranging form about 70° C. to about 130° C. Similarly, this transformation can also be carried out in NMP at about 200° C. in a microwave.

Scheme 6

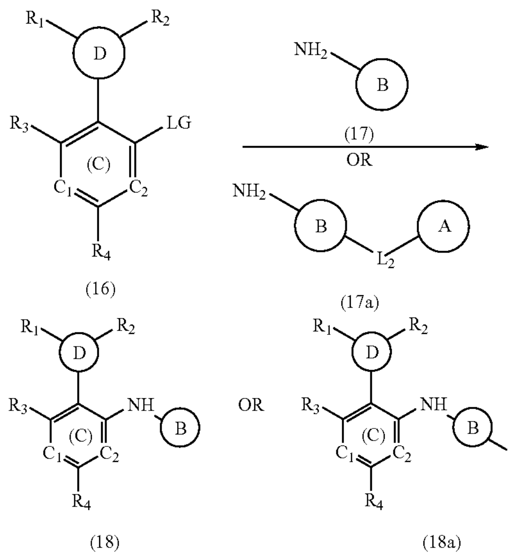

(16) (17a) (18) OR (18a)

Anilines (compound 17 or 17a) can be coupled with activated aryl chlorides (compound 16) to form biaryl anilines (compound 18 or 18a) using Pd catalysis or $NEt_3$.TFA under suitable conditions, which may or may not require the input of heat.

Alternatively, and with reference to Scheme 2, where certain $R^1$ and/or $R^2$ groups hinder or limit the ability to couple ring C to ring B via the nucleophilic displacement method described above, the B-C ring coupling can be effected from intermediate compound (6) in Scheme 2 as follows in Scheme 7.

Scheme 7

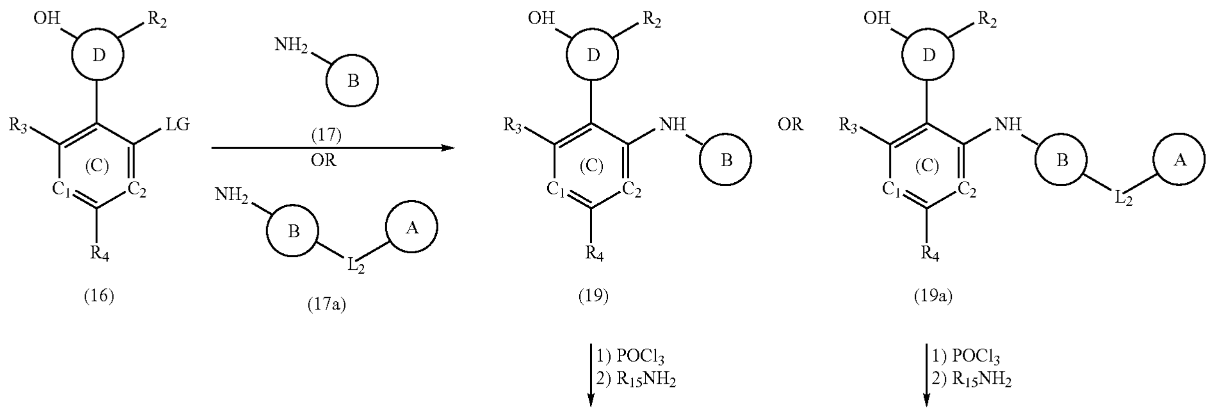

(16) (17a) (19) OR (19a)

-continued

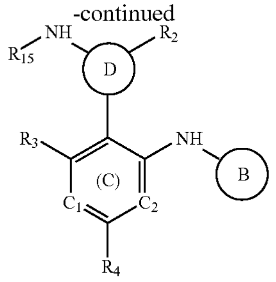

(20)

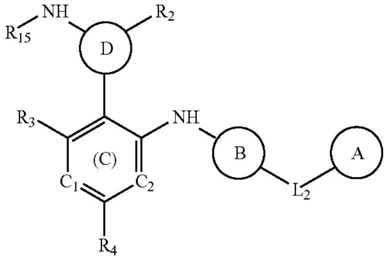

(20a)

As shown, compound (16) can first be reacted with the desired B ring nucleophilic species prior to converting the D-ring hydroxyl group to the corresponding chloride for subsequent displacement with an amine, or other desired $R^{15}$ group.

Compounds of the invention (Formulas I-III) wherein $C^1$ is $CR^{10}$ can be prepared by the general method shown in Scheme 8.

Scheme 8

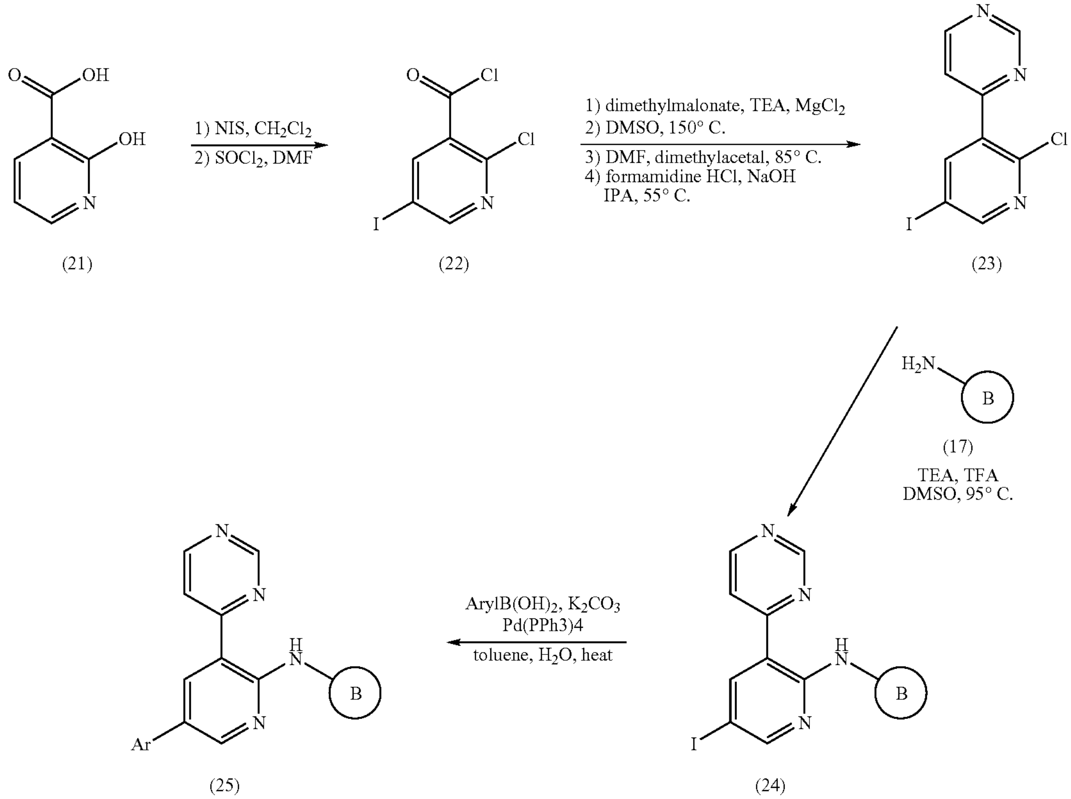

As shown, commercially available 2-hydroxynicotinic acid can be iodinated and subjected to thionyl chloride according to the procedure disclosed in Elworthy et al., J. Med. Chem., 40(17):2674-2687 (1997), which disclosure is incorporated herein by reference in its entirety. Conversion of the iodinated intermediate (compound 22) to the corresponding pyrimidine (compound 23) proceeds as described above in Scheme 2. After displacement of the pyridyl chloride (compound 23) with an aniline (compound 17) to form compound (24), Pd(0) mediated-coupling with an aryl boronate in the presence of mild base, such as sodium or potassium carbonate or bicarbonate, in toluene affords compound (25), an aryl pyridyl pyrimidine. Compound (25) can also be prepared using corresponding stannanes or zincates, as known in the art. Alternatively, desired $R^{10}$ groups may be installed onto the C-ring via the iodide, using conventional methods (not shown), as appreciated by those skilled in the art.

Alternatively, the desired aryl group can be installed on ring C (compound 20) even before building the D-C ring piece of compounds of Formulas I-III. For example, Church et al. describes the synthesis of 5-aryl-2-chloropyridines from phenylacetic acids in J. Org. Chem., 60:3750-3758 (1995), which disclosure is incorporated herein by reference in its entirety.

The following examples represent methods of synthesizing or preparing desired compounds of Formulas I-III and various structural moieties of the compounds. It should be appreciated that these examples are for illustrative purposes only and are not to be construed as limiting the scope of this invention in any manner. It should also be appreciated that other conventional, known or developed alternative methods may also be utilized to prepare compounds of Formulas I-III.

Analytical Methods:

Unless otherwise indicated, all HPLC analyses were run on a Agilent Model 1100 system with an Agilent Technologies Zorbax SB-$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 20×50 mm column at 20 mL/min. The mobile phase used a mixture of solvent A ($H_2O$/0.1% TFA) and solvent B (AcCN/0.1% TFA) with a 10 min gradient from 5% to 100% solvent B. The gradient is followed by a 2 min return to 5% AcCN.

Proton NMR Spectra:

Unless otherwise indicated, all $^1$H NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

Example 1

Synthesis of 4-(1-methyl-4-phenyl-1H-imidazol-2-ylamino)phenol

Step 1: 1-methyl-4-phenyl-1H-imidazole

To a slurry of sodium hydride, 60% in mineral oil (1.2 g, 31 mmol) in 100 mL anhyd. THF at 0° C. was added 4-phenylimidazole (4.00 g, 28 mmol) in small portions under nitrogen. Upon complete addition, the reaction was homogeneous and orange. After 10 min, methyl iodide (2.1 ml, 33 mmol) was added and the reaction was allowed to warm to ambient temperature. After 2 h, the reaction was quenched with 10 mL water and concentrated in vacuo. The resulting liquid was partitioned between water/brine and DCM. The aqueous layer was extracted with DCM (4×). The combined organic extracts were dried over anhyd sodium sulfate, filtered, and concentrated in vacuo to give an orange solid. This was dissolved in dichloromethane and purified by silica gel chromatography, 120 g, 60 min, 0-50% 90/10 DCM/MeOH in DCM, to give 1-methyl-4-phenyl-1H-imidazole and 1-methyl-5-phenyl-1H-imidazole as off-white solids.

Step 2: 2-chloro-1-methyl-4-phenyl-1H-imidazole

To a solution of 1-methyl-4-phenyl-1H-imidazole (0.600 g, 3.79 mmol) in 15 mL THF at −78° C. under nitrogen was added n-butyllithium 2.5 M in hexanes (1.67 ml, 4.17 mmol) dropwise over 3 min. The resulting orange-brown solution was allowed to stir for 30 min, at which time a solution of hexachloroethane (0.988 g, 4.17 mmol) in 5 mL THF was added slowly down the side of the flask. The orange-brown solution was allowed to stir for 1 h, and was quenched with sat'd aq. $NH_4Cl$, warmed to ambient temperature, and stirred overnight. The mixture was extracted with EtOAc, the organic layers collected and dried over anhydrous sodium sulfate, filtered, and concentrated in vacuo to give 2-chloro-1-methyl-4-phenyl-1H-imidazole as a brown solid. MS m/z=193 $[M+H]^+$. Calc'd for $C_{10}H_9N_2Cl$: 192.6.

Step 3: 4-(1-methyl-4-phenyl-1H-imidazol-2-ylamino)phenol

A slurry of 4-aminophenol (0.227 g, 2.08 mmol), 2-chloro-1-methyl-4-phenyl-1H-imidazole (0.400 g, 2.08 mmol), and p-toluenesulfonic acid monohydrate (0.395 g, 2.08 mmol) was heated in 2.5 mL 2-BuOH in a sealed tube to about 110° C. for 24 h. The temperature was increased to about 120° C. and the solution was heated for 24 h. The reaction was cooled and partitioned between 50 mL pH7 buffer and DCM. The aqueous layer was extracted with DCM (3×), and the combined organics were dried over anhydrous sodium sulfate, filtered, and concentrated in vacuo. The resulting brown oil was purified by silica gel chromatography (0-100% 90/10 DCM/MeOH in DCM) to give 4-(1-methyl-4-phenyl-1H-imidazol-2-ylamino)phenol as a tan solid. MS m/z=266 $[M+H]^+$. Calc'd for $C_{16}H_{15}N_3O$: 265.3.

Example 2

Synthesis of N1-(2-(dimethylamino)ethyl)benzene-1,2-diamine

Step 1: N-(2-(dimethylamino)ethyl)-2-nitrobenzenamine

To a mixture of 2-fluoronitrobenzene (2.0 g, 14 mmol) and sodium bicarbonate (5.9 g, 71 mmol) in 30 mL THF under nitrogen was added N1, N1-dimethylethane-1,2-diamine (1.7 mL, 16 mmol). The reaction was allowed to stir at ambient temperature for 3 h, and then a water-cooled reflux condenser was added and the mixture was heated to 70° C. for 16 h. The reaction was cooled to ambient temperature, filtered through paper, and concentrated in vacuo to give N-(2-(dimethylamino)ethyl)-2-nitrobenzenamine as a yellow oil. This material was used without further purification.

Step 2: N1-(2-(dimethylamino)ethyl)benzene-1,2-diamine

N-(2-(dimethylamino)ethyl)-2-nitrobenzenamine (2.0 g, 14 mmol) and 10% palladium on carbon, wet, 50% water (3.0 g) were combined under nitrogen. 30 mL MeOH was added via syringe, and the atmosphere was replaced with hydrogen from a balloon. The reaction was stirred rapidly for 20 h, at which point the reaction was flushed with nitrogen, and filtered through a pad of Celite®, and concentrated in vacuo to give N1-(2-(dimethylamino)ethyl)benzene-1,2-diamine as a red-brown solid. This material was used without further purification. MS m/z=180 $[M+H]^+$. Calc'd for $C_{10}H_{17}N_3$: 179.3.

Example 3

Synthesis of N1-(3-(dimethylamino)propyl)benzene-1,2-diamine

The title compound was synthesized in a manner analogous to that described in Example 2. MS m/z=194 $[M+H]^+$. Calc'd for $C_{11}H_{19}N_3$: 193.3.

Example 4

Method A

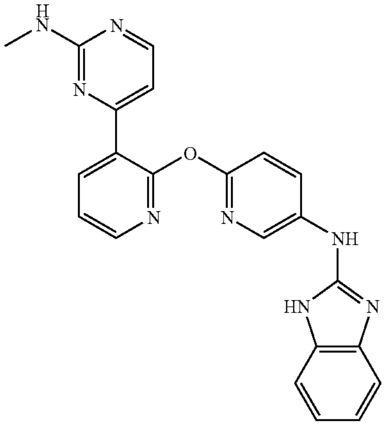

Synthesis of N-(6-(3-(2-(methylamino)pyrimidin-4-yl)pyridin-2-yloxy)pyridin-3-yl)-1H-benzo[d]imidazol-2-amine Step 1: 4-(2-(4-isothiocyanatophenoxy)phenyl)-N-methylpyrimidin-2-amine To a slurry of 4-(2-(4-aminophenoxy)phenyl)-N-methylpyrimidin-2-amine (0.300 g, 1.03 mmol) in MC was added di-2-pyridyl thionocarbonate (0.227 g, 0.977 mmol). The orange reaction was allowed to stir overnight, and was then diluted with MC and washed $4\times H_2O$. The organic layer was dried over anhyd. $Na_2SO_4$, filtered, and concentrated in vacuo to give 4-(2-(4-isothiocyanatophenoxy)phenyl)-N-methylpyrimidin-2-amine as an off-white solid. This material was used without further purification. MS m/z=335 $[M+H]^+$. Calc'd for $C_{18}H_{14}N_4OS$: 334.4.

Step 2: N-(6-(3-(2-(methylamino)pyrimidin-4-yl)pyridin-2-yloxy)pyridin-3-yl)-1H-benzo[d]imidazol-2-amine A mixture of benzene-1,2-diamine (0.091 g, 0.85 mmol), 4-(2-(5-isothiocyanatopyridin-2-yloxy)pyridin-3-yl)-N-methylpyrimidin-2-amine (0.237 g, 0.70 mmol), and polymer-supported carbodiimide (Argonaut technologies, 1.6 mmol/g, 1.3 g, 2.1 mmol) was heated for 14 h in anhydrous THF in a sealed vial. The reaction was cooled and was filtered, rinsing with 100 mL DCM. The filtrate was concentrated in vacuo to give an off-white solid. Sonication in dichloromethane gave a fluffy precipitate, which was filtered and collected to give an off-white solid. This material was adsorbed onto 0.8 g SiO2 from MeOH/MC, and purified by silica gel chromatography, 40 g, 0-10% MeOH/MC to give N-(6-(3-(2-(methylamino)pyrimidin-4-yl)pyridin-2-yloxy)pyridin-3-yl)-1H-benzo[d]imidazol-2-amine as a white solid MS m/z=411 $[M+H]^+$. Calc'd for $C_{22}H_{18}N_8O$: 410.4.

Example 5

Method B1

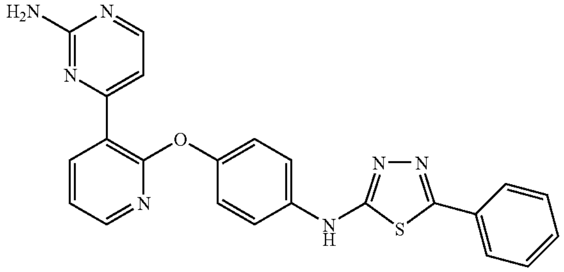

Synthesis of 4-(2-(4-(5-phenyl-1,3,4-thiadiazol-2-ylamino)phenoxy)pyridin-3-yl)pyrimidin-2-amine A slurry of pyridinium p-toluenesulfonate (0.18 g, 0.72 mmol), 4-(2-(4-aminophenoxy)pyridin-3-yl)pyrimidin-2-amine (0.100 g, 0.36 mmol), and 2-chloro-5-phenyl-1,3,4-thiadiazole (0.077 g, 0.39 mmol; prepared by method described in J. Med. Chem., 31:902 (1988)) was heated in 2 mL 2-BuOH in a sealed tube to 110° C. The reaction became dark brown and homogeneous. After 2 h the reaction was quenched with 1N NaOH and DCM. The aqueous layer was extracted 2×DCM, and the emulsified aqueous layer was filtered and rinsed with dichloromethane. The resulting solid was adsorbed onto silica gel from MeOH/DCM, dried, and purified by silica gel chromatography, 0-100% 90/10 DCM/MeOH in DCM to give 4-(2-(4-(5-phenyl-1,3,4-thiadiazol-2-ylamino)phenoxy)pyridin-3-yl)pyrimidin-2-amine as a white solid. MS m/z=440 $[M+H]^+$. Calc'd for $C_{23}H_{17}N_7OS$: 439.5.

Example 6

Method B2

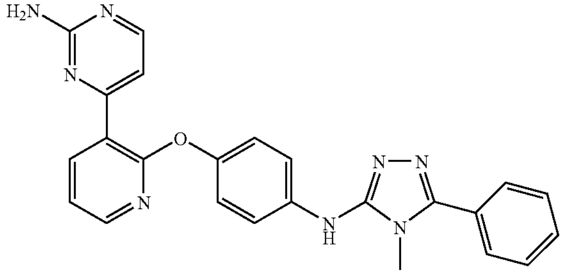

Synthesis of 4-(2-(4-(4-methyl-5-phenyl-4H-1,2,4-triazol-3-ylamino)phenoxy)pyridin-3-yl)pyrimidin-2-amine Step 1: 4-methyl-3-(methylthio)-5-phenyl-4H-1,2,4-triazole To a solution of 4-methyl-5-phenyl-4H-1,2,4-triazole-3-thiol (2.00 g, 10 mmol) in NaOH 1.0 M in $H_2O$ (21 ml, 21 mmol) was added a solution of $CH_3I$ (0.98 mL, 16 mmol) in 6 mL EtOH. The reaction became cloudy and then clear. After 15 min, a white solid precipitated out of the reaction. The reaction was filtered, rinsing with water. The solid was collected and dried in vacuo to give 4-methyl-3-(methylthio)-5-phenyl-4H-1,2,4-triazole as a white solid. MS m/z=206 $[M+H]^+$. Calc'd for $C_{10}H_{11}N_3S$: 205.3.

Step 2: 4-methyl-3-(methylsulfonyl)-5-phenyl-4H-1,2,4-triazole

A slurry of 4-methyl-3-(methylthio)-5-phenyl-4H-1,2,4-triazole (0.360 g, 1.75 mmol) and oxone(r) monopersulfate compound (2.16 g, 3.51 mmol) were stirred rapidly in 5 mL MeOH overnight. The reaction was concentrated and the solids diluted with water, ice, and treated with 6 N NaOH until a pH>10. The resulting material was extracted 3×DCM, and the combined organic layers were dried over anhyd sodium sulfate, filtered, and concentrated to give 4-methyl-3-(methylsulfonyl)-5-phenyl-4H-1,2,4-triazole as a white solid. MS m/z=238 $[M+H]^+$. Calc'd for $C_{10}H_{11}N_3O_2S$: 237.3.

Step 3: 4-(2-(4-(4-methyl-5-phenyl-4H-1,2,4-triazol-3-ylamino)phenoxy)pyridin-3-yl)pyrimidin-2-amine To a slurry of 4-(2-(4-aminophenoxy)pyridin-3-yl)pyrimidin-2-amine (0.150 g, 0.54 mmol) and 4-methyl-3-(methylsulfonyl)-5-phenyl-4H-1,2,4-triazole (0.14 g, 0.59 mmol) in 0.6 mL THF was added lithium bis(trimethylsilyl) amide, 1.0 m solution in tetrahydrofuran (1.1 ml, 1.1 mmol). The reaction became a solid, and was sealed and heated to 70° C., at which point it became a heterogeneous brown mixture that could be stirred. After 2 h, the reaction did not appear to make further progress. The reaction was quenched with sat'd aqueous $NH_4Cl$ and partitioned between DCM and water. The aqueous layer was extracted 1×DCM. The combined organic layers were dried over anhydrous sodium sulfate, filtered, and concentrated in vacuo. The material was absorbed onto silica gel from MeOH/DCM and dried. The residue was purified by silica gel chromatography, 40 g (0-100% 90/10 DCM/MeOH in MC) to give 4-(2-(4-(4-methyl-5-phenyl-4H-1,2,4-triazol-3-ylamino)phenoxy)pyridin-3-yl)pyrimidin-2-amine as a white solid. MS m/z=437 $[M+H]^+$. Calc'd for $C_{24}H_{20}N_8O$: 436.5.

Example 7

Method B3

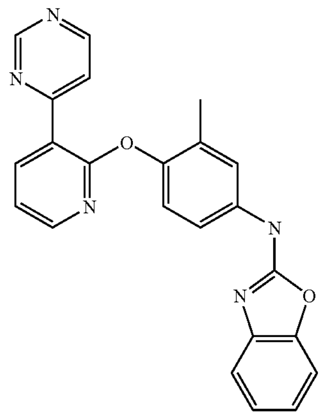

Synthesis of N-(3-methyl-4-(3-(pyrimidin-4-yl)pyridin-2-yloxy)phenyl)benzo[d]oxazol-2-amine To 3-methyl-4-(3-(pyrimidin-4-yl)pyridin-2-yloxy)benzenamine (30 mg, 0.11 mmol) in toluene (2.0 mL) was added 2-chlorobenzo[d]oxazole (0.014 mL, 0.12 mmol). The resulting mixture was heated to 100° C. for 47 h. The mixture was diluted with DMSO and purified by Gilson reverse-phase HPLC. The product-containing fractions were combined, diluted with methylene chloride, and extracted with saturated sodium carbonate. The organic layer was dried over anhydrous sodium sulfate, filtered, and concentrated to yield the title compound as a tan solid. MS m/z=396 $[M+H]^+$. Calc'd for $C_{23}H_{17}N_6O_2$: 395.42.

Example 8

Method C

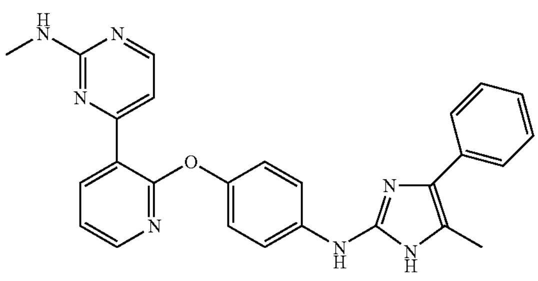

Synthesis of N-methyl-4-(2-(4-(5-methyl-4-phenyl-1H-imidazol-2-ylamino)phenoxy)pyridin-3-yl)pyrimidin-2-amine Step 1: 1-(4-(3-(2-(methylamino)pyrimidin-4-yl)pyridin-2-yloxy)phenyl)guanidine bis-t-butylcarbamate To a dark solution of 4-(2-(4-aminophenoxy)pyridin-3-yl)-N-methylpyrimidin-2-amine (0.750 g, 2.6 mmol) in DMF was added TEA (1.1 ml, 7.9 mmol) and 1,3-bis(tert-butoxycarbonyl)-2-methyl-2-thiopseudourea (0.78 g, 2.7 mmol) followed by mercury(ii) chloride (0.80 g, 2.9 mmol). Upon addition of the mercury, the reaction became very thick and difficult to stir. The reaction was allowed to stir overnight, and was then diluted with DCM and 2 N sodium carbonate solution. The mixture was filtered through a 2 cm Celite® pad in a glass frit, rinsing with water and dichloromethane. The organic layer was washed three times with water, dried over sodium sulfate, filtered, and concentrated in vacuo. The resulting brown oil was purified by silica gel chromatography, 80 g, 0-30% 90/10 MC/MeOH in MC, to give 1-(4-(3-(2-(methylamino)pyrimidin-4-yl)pyridin-2-yloxy)phenyl)guanidine bis-t-butylcarbamate as a peach-colored solid. MS m/z=536 $[M+H]^+$. Calc'd for $C_{27}H_{33}N_7O_5$: 535.6.

Step 2: 1-(4-(3-(2-(methylamino)pyrimidin-4-yl)pyridin-2-yloxy)phenyl)guanidine bis-TFA salt To an orange solution of 1-(4-(3-(2-(methylamino)pyrimidin-4-yl)pyridin-2-yloxy)phenyl)guanidine bis-t-butylcarbamate (1.1 g, 2.1 mmol) in 15 mL DCM under nitrogen at 0° C. was added TFA (3.1 ml, 41 mmol). The reaction was allowed to warm to ambient temperature and was allowed to stir overnight. The reaction was concentrated in vacuo to give 1-(4-(3-(2-(methylamino)pyrimidin-4-yl)pyridin-2-yloxy)phenyl)guanidine bis-TFA salt as a brown oil, which was used without further purification. MS m/z=336 $[M+H]^+$. Calc'd for $C_{17}H_{17}N_7O$: 335.2.

Step 3: N-methyl-4-(2-(4-(5-methyl-4-phenyl-1H-imidazol-2-ylamino)phenoxy)pyridin-3-yl)pyrimidin-2-amine To a mixture of 1-(4-(3-(2-(methylamino)pyrimidin-4-yl)pyridin-2-yloxy)phenyl)guanidine bis-TFA salt (0.200 g, 0.35 mmol) and potassium carbonate (0.20 g, 1.4 mmol) in 1 mL DMSO was added 2-bromo-1-phenylpropan-1-one (0.054 ml, 0.35 mmol). The reaction was allowed to stir at ambient temperature for 30 min, then 70° C. After 16 h, the reaction was quenched by addition of water and was extracted with EtOAc. The organic layer was dried over anhyd. Sodium sulfate, filtered, and concentrated in vacuo. The resulting green/brown oil was purified by silica gel chromatography (40 g, 0-100% 90/10 MC/MeOH in MC) to give an oil. This was lyophilized from MeOH/water to give N-methyl-4-(2-(4-(5-methyl-4-phenyl-1H-imidazol-2-ylamino)phenoxy)pyridin-3-yl)pyrimidin-2-amine as an off-white solid. MS m/z=450 $[M+H]^+$. Calc'd for $C_{26}H_{23}N_7O$: 449.5.

Example 9

Method D

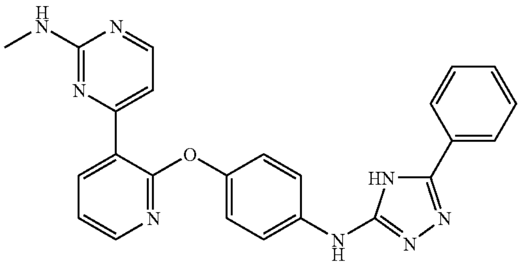

Synthesis of N-methyl-4-(2-(4-(5-phenyl-4H-1,2,4-triazol-3-ylamino)phenoxy)pyridin-3-yl)pyrimidin-2-amine Step 1: 1-benzoyl-2-methyl-3-(4-(3-(2-(methylamino)pyrimidin-4-yl)pyridin-2-yloxy)phenyl)isothiourea To a heterogeneous brown mixture of 4-(2-(4-aminophenoxy)pyridin-3-yl)-N-methylpyrimidin-2-amine (0.260 g, 0.886 mmol) in 2 mL acetone was added benzoyl isothiocyanate (0.136 ml, 0.975 mmol) dropwise via syringe. The mixture became homogeneous and remained brown. After 10 min, a precip formed. After 16 h, iodomethane (0.0554 ml, 0.886 mmol) was added, and the reaction was heated to 80° C. The mixture became homogeneous. After 3 h, further iodomethane (0.0554 ml, 0.886 mmol) was added and after 1 h at 80° C. and 3 days at ambient temperature, the reaction was adsorbed onto 1.7 g $SiO_2$ and dried. The solid was purified by silica gel chromatography, 40 g, 0-10% MeOH/MC, to give 1-benzoyl-2-methyl-3-(4-(3-(2-(methylamino)pyrimidin-4-yl)pyridin-2-yloxy)phenyl)isothiourea which was used without further purification. MS m/z=471 $[M+H]^+$. Calc'd for $C_{25}H_{22}N_6O_2$: 470.5.

Step 2: N-methyl-4-(2-(4-(5-phenyl-4H-1,2,4-triazol-3-ylamino)phenoxy)pyridin-3-yl)pyrimidin-2-amine A slurry of 1-benzoyl-2-methyl-3-(4-(3-(2-(methylamino)pyrimidin-4-yl)pyridin-2-yloxy)phenyl)isothiourea (0.174 g, 0.37 mmol) and anhydrous hydrazine (0.35 ml, 11 mmol) in EtOH was sealed and heated to 80° C. After 16 h, a yellow precipitate formed. The reaction was cooled to ambient temperature, filtered, rinsing with 2×1 mL EtOH, and the solid was dried in vacuo to give N-methyl-4-(2-(4-(5-phenyl-4H-

1,2,4-triazol-3-ylamino)phenoxy)pyridin-3-yl)pyrimidin-2-amine as a white solid. MS m/z=437 $[M+H]^+$. Calc'd for $C_{24}H_{20}N_8O$: 436.5.

Example 10

Method E

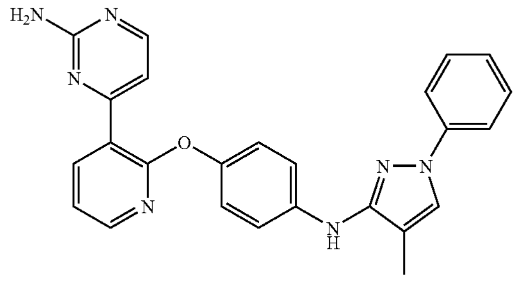

Synthesis of 4-(2-(4-(4-methyl-1-phenyl-1-H-pyrazol-3-ylamino)phenoxy)pyridin-3-yl)pyrimidin-2-amine Step 1. Preparation of N-(4-methoxyphenal)-4-methyl-1-phenyl-4,5-dihydro-1H-pyrazol-3-amine A 100 ml round bottom flask was charged with 4-methyl-1-phenyl-4,5-dihydro-1H-pyrazol-3-ol (1.00 g, 5.68 mmol), 4-methoxybenzenamine (2.27 g, 18.44 mmol), and p-toluenesulfonic acid monohydrate (0.59 g, 3.12 mmol). The reaction mixture was stirred at 140° C. under a nitrogen atmosphere for 16 h. The reaction was cooled and dissolved in 1% NaOH solution and ether. The organic layer was separated, washed with 1% HCl solution and water, then dried over $Na_2SO_4$, filtered, and concentrated to afford N-(4-methoxyphenyl)-4-methyl-1-phenyl-4,5-dihydro-1-H-pyrazol-3-amine as a brown solid. MS m/z=282.2 $[M+H]^+$. Calc'd for $C_{17}H_{19}N_3O$: 281.35.

Step 2. Preparation of N-(4-methoxyphenyl)-4-methyl-1-phenyl-1H-pyrazol-3-amine

A 200 ml round bottom flask, under nitrogen, was charged with N-(4-methoxyphenyl)-4-methyl-1-phenyl-4,5-dihydro-1H-pyrazol-3-amine (0.85 g, 3.02 mmol) and DCM (60.42 ml, 0.05 M). To this solution was added slowly manganese dioxide (0.58 g, 6.65 mmol). Reaction stirred at RT under a nitrogen atmosphere for 16 h. The reaction mixture was diluted with DCM and filtered over Celite®. The filtrate was concentrated to afford brown oil, which was purified by ISCO silica gel chromatography (20-40% EtOAc/hexanes) to afford N-(4-methoxyphenyl)-4-methyl-1-phenyl-1H-pyrazol-3-amine. MS m/z=280.2 $[M+H]^+$. Calc'd for $C_{17}H_{17}N_3O$: 279.34.

Step 3. Preparation of 4-(4-methyl-1-phenyl-1H-pyrazol-3-ylamino)phenol

A 50 ml round bottom flask was charged with N-(4-methoxyphenyl)-4-methyl-1-phenyl-1H-pyrazol-3-amine (0.37 g, 1.33 mmol), hydrobromic acid (2.16 ml, 39.74 mmol), and acetic acid (2.27 ml, 39.74 mmol). The reaction mixture was stirred at 110° C. for 4 h, then cooled to RT and diluted with water. The solution was neutralized with 6 N NaOH until a pH of about 6, upon which the product precipitated out of solution. The solid was filtered and dried under high vacuum to afford 4-(4-methyl-1-phenyl-1H-pyrazol-3-ylamino)phenol as a dark solid. MS m/z=266.1 $[M+H]^+$. Calc'd for $C_{16}H_{15}N_3O$: 265.31.

Step 4. Preparation of 4-(2-(4-(4-methyl-1-phenyl-1H-pyrazol-3-ylamino)phenoxy)pyridin-3-yl)pyrimidin-2-amine A resealable reaction tube was charged with 4-(4-methyl-1-phenyl-1H-pyrazol-3-ylamino)phenol (0.12 g, 0.45 mmol), 4-(2-chloropyridin-3-yl)pyrimidin-2-amine (0.09 g, 0.45 mmol), cesium carbonate (0.30 g, 0.91 mmol), and DMSO (2.26 ml, 0.2 M). The reaction vessel was sealed and the mixture stirred at 130° C. for 16 h. The reaction was cooled to RT, diluted with 1 ml DMSO and passed through a PTFE acrodisc filter via syringe. The residue was purified by Gilson reverse phase chromatography (10% to 90% $CH_3CN/H_2O/0.1\%$ TFA), and the product-containing fractions were combined, basified by addition of aq. $NaHCO_3$ and extracted with ethyl acetate. The organic portion was dried with $Na_2SO_4$, filtered, and concentrated to afford pure 4-(2-(4-(4-methyl-1-phenyl-1H-pyrazol-3-ylamino)phenoxy)pyridin-3-yl)pyrimidin-2-amine as a tan solid. MS m/z=436.2 $[M+H]^+$. Calc'd for $C_{25}H_{21}N_7O$: 435.48.

Example 11

Method F1

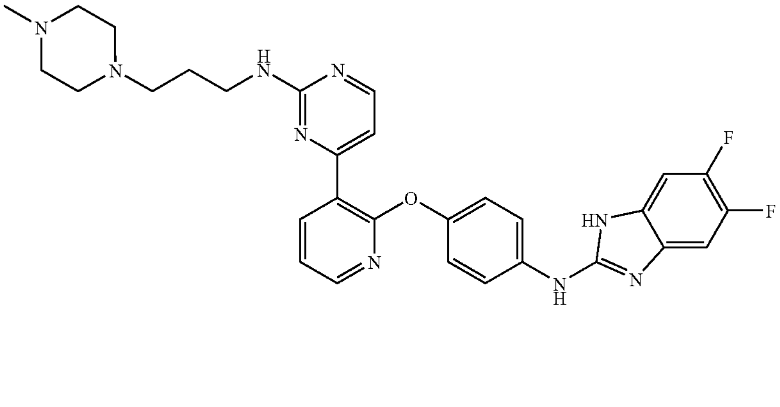

Synthesis of 5,6-difluoro-N-(4-(3-(2-(3-(4-methylpiperazin-1-yl)propylamino)pyrimidin-4-yl)pyridin-2-yloxy)phenyl)-1H-benzo[d]imidazol-2-amine Step 1. Preparation of 4-(3-(2-(methylthio)pyrimidin-4-yl)pyridin-2-yloxy)benzenamine A resealable pressure bottle was charged with 4-(2-chloropyridin-3-yl)-2-(methylthio)pyrimidine (2.85 g, 12.00 mmol), 4-aminophenol (1.44 g, 26.5 mmol), and cesium carbonate (1.44 g, 13.20 mmol). These reagents were suspended in DMSO (24 ml, 0.50 M), and the vessel was sealed and mixture heated to 130° C. for 48 h. The reaction mixture was allowed to cool to RT, diluted with water and extracted with ethyl acetate. The organic layer was collected, dried with $Na_2SO_4$, filtered, and concentrated to give light brown residue, which was purified by silica gel chromatography (ISCO, 10% to 50% Ethyl Acetate/Hexanes) to afford 4-(3-(2-(methylthio)pyrimidin-4-yl)pyridin-2-yloxy)benzenamine as a light yellow solid. MS m/z=311 [M+H]$^+$. Calc'd for $C_{16}H_{14}N_4OS$: 310.37.

Step 2. Preparation of 4-(2-(4-isothiocyanatophenoxy)pyridin-3-yl)-2-(methylthio)pyrimidine A dry 100 ml round bottom flask, under nitrogen, was charged with 4-(3-(2-(methylthio)pyrimidin-4-yl)pyridin-2-yloxy) benzenamine (1.72 g, 5.54 mmol), O,O-dipyridin-2-yl carbonothioate (1.35 g, 5.82 mmol), and DCM (37 ml, 0.15 M). The vessel was closed, kept under nitrogen, and mixture stirred at RT for 18 h. The reaction was diluted with 20 ml DCM and washed with water. The organic layer was collected, dried with $Na_2SO_4$, filtered, and concentrated to give 4-(2-(4-isothiocyanatophenoxy)pyridin-3-yl)-2-(methylthio)pyrimidine as a yellow solid. MS m/z=353.0 [M+H]$^+$. Calc'd for $C_{17}H_{12}N_4OS_2$: 352.43.

Step 3. Preparation of 5,6-difluoro-N-(4-(3-(2-(methylthio)pyrimidin-4-yl)pyridin-2-yloxy)phenyl)-1H-benzo[d]imidazol-2-amine A resealable pressure vial, under nitrogen, was charged with 4-(2-(4-isothiocyanatophenoxy)pyridin-3-yl)-2-(methylthio)pyrimidine (1.12 g, 3.18 mmol), PS-DCC (1.27 mmol/g polymer supported cyclohexyl carbodiimide) (7.50 g, 9.53 mmol), 4,5-difluorobenzene-1,2-diamine (0.69 g, 4.77 mmol), and THF (45 ml, 0.07 M). The vessel was sealed and the reaction mixture stirred at 70° C. for 4 h. The reaction mixture was cooled to RT, diluted with DCM, and filtered over celite. The filtrate was concentrated to afford yellow residue, which was triturated with DCM, filtered, and dried under high vacuum to afford 5,6-difluoro-N-(4-(3-(2-(methylthio)pyrimidin-4-yl)pyridin-2-yloxy)phenyl)-1H-benzo[d]imidazol-2-amine as a tan solid. MS m/z=463.1 [M+H]$^+$. Calc'd for $C_{23}H_{16}F_2N_6OS$: 462.48.

Step 4. Preparation of 5,6-difluoro-N-(4-(3-(2-(methylsulfonyl)pyrimidin-4-yl)pyridin-2-yloxy)phenyl)-1H-benzo[d]imidazol-2-amine A 100 ml dry round bottom flask was charged with 5,6-difluoro-N-(4-(3-(2-(methylthio)pyrimidin-4-yl)pyridin-2-yloxy)phenyl)-1H-benzo[d]imidazol-2-amine (0.82 g, 1.76 mmol) and sonicated in methanol (17.62 ml, 0.10 M) for 20 minutes. To this was added oxone (3.25 g, 5.29 mmol) and mixture stirred at RT for 2 days. The reaction mixture was cooled to 0° C. and basified with aq. $NaHCO_3$. The resulting solids were filtered, washed with water, and dried under high vacuum to provide 5,6-difluoro-N-(4-(3-(2-(methylsulfonyl)pyrimidin-4-yl)pyridin-2-yloxy)phenyl)-1H-benzo[d]imidazol-2-amine as a light yellow solid. MS m/z=495.1 [M+H]$^+$. Calc'd for $C_{23}H_{16}F_2N_6O_3S$: 494.47.

Step 5. Preparation of 5,6-difluoro-N-(4-(3-(2-(3-(4-methylpiperazin-1-yl)propylamino)pyrimidin-4-yl)pyridin-2-yloxy)phenyl)-1H-benzo[d]imidazol-2-amine A resealable pressure vial was charged with 5,6-difluoro-N-(4-(3-(2-(methylsulfonyl)pyrimidin-4-yl)pyridin-2-yloxy)phenyl)-1H-benzo[d]imidazol-2-amine (0.14 g, 0.28 mmol), 3-(4-methylpiperazin-1-yl)propan-1-amine (0.18 g, 1.13 mmol), and 2-propanol (1.89 ml, 0.15 M). The reaction vessel was sealed and the mixture stirred at 70° C. for 16 h. The reaction mixture was cooled to RT, diluted with DCM, and washed with Aq. $NaHCO_3$. The organic layer was collected, dried over $Na_2SO_4$, and concentrated to afford brown residue, which was purified by Gilson reverse phase chromatography (10% to 90% $CH_3CN/H_2O$/0.1% TFA). The product-containing fractions were combined, basified by addition of aq. $NaHCO_3$ and extracted with ethyl acetate. The organic portion was dried with $Na_2SO_4$, filtered, and concentrated to afford pure 5,6-difluoro-N-(4-(3-(2-(3-(4-methylpiperazin-1-yl)propylamino)pyrimidin-4-yl)pyridin-2-yloxy)phenyl)-1H-benzo[d]imidazol-2-amine as a yellow solid. MS m/z=572.2 [M+H]$^+$. Calc'd for $C_{30}H_{31}F_2N_9O$: 571.62.

Example 12

Method F2

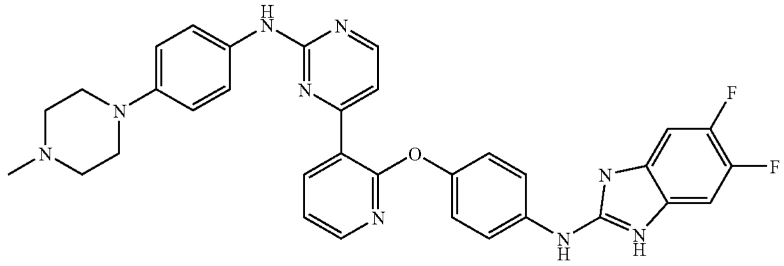

Synthesis of 5,6-difluoro-N-(4-(3-(2-(4-(4-methylpiperazin-1-yl)phenylamino)pyrimidin-4-yl)pyridin-2-yloxy)phenyl)-1-H-benzo[d]imidazol-2-amine A resealable pressure bottle, under nitrogen, was charged with 5,6-difluoro-N-(4-(3-(2-(methylsulfonyl)pyrimidin-4-yl)pyridin-2-yloxy)phenyl)-1H-benzo[d]imidazol-2-amine (0.13 g, 0.26 mmol), 4-(4-methylpiperazin-1-yl)benzenamine (0.25 g, 1.31 mmol), TFA (0.12 ml, 1.58 mmol), and 2-propanol (10.00 ml, 0.03 M). The reaction vessel was sealed and the mixture stirred at 90° C. for 4 days. The reaction mixture was cooled to RT and concentrated to brown residue. The residue was purified by Biotage silica gel chromatography (2%-8% MeOH/Dichloromethane) followed by Gilson reverse phase chromatography (10% to 90% $CH_3CN/H_2O$/0.1% TFA). The product-containing fractions were combined, basified by addition of aq. $NaHCO_3$ and extracted with ethyl acetate. The organic portion was dried with $Na_2SO_4$, filtered, and concentrated to afford 5,6-difluoro-N-(4-(3-(2-(4-(4-methylpiperazin-1-yl)phenylamino)pyrimidin-4-yl)pyridin-2-yloxy)phenyl)-1H-benzo[d]imidazol-2-amine as a yellow solid. MS m/z=606.1 $[M+H]^+$. Calc'd for $C_{33}H_{29}F_2N_9O$: 605.64.

Example 13

Method F3

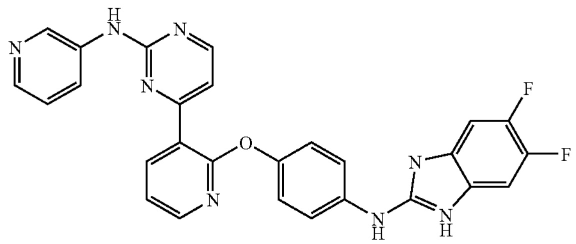

Synthesis of 5,6-difluoro-N-(4-(3-(2-(pyridin-3-ylamino)pyrimidin-4-yl)pyridin-2-yloxy)phenyl)-1H-benzo[d]imidazol-2-amine A resealable reaction vial, under nitrogen, was charged with pyridin-3-amine (0.04 g, 42.50 mmol) and DMF (0.80 ml, 0.1 M). This was cooled to 0° C. and 60% wt in oil sodium hydride added (0.01 g, 42.50 mmol). The reaction mixture was stirred at 0° C. under a nitrogen atmosphere for 35 min. 5,6-Difluoro-N-(4-(3-(2-(methylsulfonyl)pyrimidin-4-yl)pyridin-2-yloxy)phenyl)-1H-benzo[d]imidazol-2-amine (0.04 g, 0.08 mmol) was added slowly to the mixture which was allowed to warm up to RT and stirred for 1 hr. The reaction mixture was heated to 60° C. and stirred for 1 hr. The reaction mixture was cooled to RT, then diluted with water and ethyl acetate. The layers were separated, the organic layer was dried over sodium sulfate and concentrated under reduced pressure to give oily residue, which was purified by silica prep plate (0.5% $NH_4OH$/9.5% MeOH/Dichloromethane) followed by Gilson reverse phase chromatography (10% to 90% $CH_3CN/H_2O$/0.1% TFA) to afford 5,6-difluoro-N-(4-(3-(2-(pyridin-3-ylamino)pyrimidin-4-yl)pyridin-2-yloxy)phenyl)-1H-benzo[d]imidazol-2-amine as a yellow solid. MS m/z=509.0 $[M+H]^+$. Calc'd for $C_{27}H_{18}F_2N_8O$: 508.48.

Example 14

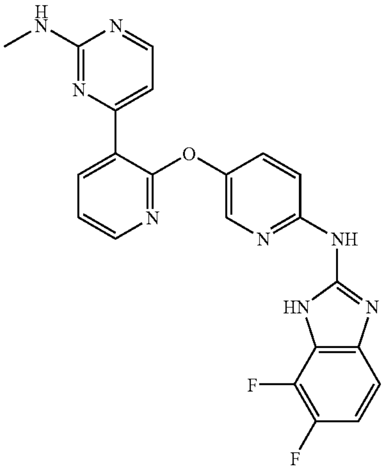

Synthesis of 6,7-difluoro-N-(5-(3-(2-(methylamino)pyrimidin-4-yl)pyridin-2-yloxy)pyridin-2-yl)-1H-benzo[d]imidazol-2-amine Step 1: 4-(2-(6-chloropyridin-3-yloxy)pyridin-3-yl)-2-(methylthio)pyrimidine A mixture of cesium carbonate (5.03 g, 15.4 mmol), 6-chloropyridin-3-ol (1.00 g, 7.72 mmol), and 4-(2-chloropyridin-3-yl)-2-(methylthio)pyrimidine (1.83 g, 7.72 mmol) was sealed and heated to 120° C. overnight. The reaction was cooled slightly and poured slowly into a rapidly stirring solution of 250 mL water. A tan precipitate resulted which was collected by filtration through a 0.45 micron filter. The solid was washed 3× with water, then dried in vacuo overnight to give 4-(2-(6-chloropyridin-3-yloxy)pyridin-3-yl)-2-(methylthio)pyrimidine as a tan solid. MS m/z=331 $[M+H]^+$. Calc'd for $C_{15}H_{11}ClN_4OS$: 330.8.

Step 2: 5-(3-(2-(methylthio)pyrimidin-4-yl)pyridin-2-yloxy)pyridin-2-amine

To a brown solution of tris(dibenzylideneacetone)dipalladium (o) (0.68 g, 0.75 mmol), 2-(dicyclohexylphosphino)biphenyl (0.50 g, 1.4 mmol), and 4-(2-(6-chloropyridin-3-yloxy) pyridin-3-yl)-2-(methylthio)pyrimidine (1.9 g, 5.7 mmol) in 15 mL dioxane was added solid lithium bis(trimethylsilyl) amide (2.9 g, 17 mmol). Argon was bubbled through the reaction for 1 min, and then it was sealed and heated to 65° C. for 3.5 days. The reaction was cooled to ambient temperature, diluted with water, and acidified to a pH of about 1 with stirring, then brought to pH of about 5 with 6N NaOH. Dichloromethane was added and reaction was filtered through 2 cm Celite® in a frit, rinsing with MC and water. The layers were separated, and the organic layer was dried over anhyd. $Na_2SO_4$, filtered, and concentrated in vacuo. The material was diluted in 100 mL MC, and extracted 3×100 mL 1 N HCl. The aqueous layers were cooled to 0° C. and basified with 6 N NaOH to about pH of 10. The aqueous layer was extracted 3×100 mL with MC. The organic layers were combined, dried over anhdrous sodium sulfate, filtered, and concentrated in vacuo to a brown oil. The oil residue was purified by silica gel chromatography, 120 g, 0-50% MC-90/10 MC/MeOH, to afford 5-(3-(2-(methylthio)pyrimidin-4-yl) pyridin-2-yloxy)pyridin-2-amine as a yellow solid. MS m/z=312 $[M+H]^+$. Calc'd for $C_{15}H_{13}N_5OS$: 311.4.

Step 3: 4-(2-(6-isothiocyanatopyridin-3-yloxy)pyridin-3-yl)-2-(methylthio)pyrimidine To a mixture of 5-(3-(2-(methylthio)pyrimidin-4-yl)pyridin-2-yloxy)pyridin-2-amine (0.170 g, 0.546 mmol) in DCM was added di-2-pyridyl thionocarbonate (0.133 g, 0.573 mmol). The reaction was allowed to stir overnight. After 16 h, the reaction was washed 4× with water, then transferred to a separatory funnel and diluted with DCM. The organic layer was washed with water, dried over anhydrous sodium sulfate, filtered, and concentrated in vacuo to give 4-(2-(6-isothiocyanatopyridin-3-yloxy)pyridin-3-yl)-2-(methylthio)pyrimidine. MS m/z=354 $[M+H]^+$. Calc'd for $C_{16}H_{11}N_5OS_2$: 353.4.

Step 4: 6,7-difluoro-N-(5-(3-(2-(methylthio)pyrimidin-4-yl)pyridin-2-yloxy)pyridin-2-yl)-1H-benzo[d]imidazol-2-amine A mixture of 4-(2-(6-isothiocyanatopyridin-3-yloxy)pyridin-3-yl)-2-(methylthio)pyrimidine (0.205 g, 0.580 mmol), 3,4-difluorobenzene-1,2-diamine (0.100 g, 0.696 mmol), and polymer-supported carbodiimide (1.34 g, 1.74 mmol, 1.3 mmol/g) in THF was heated in a sealed vial. After 4 h, the reaction was cooled slightly and filtered, rinsing with 100 mL DCM. The filtrate was concentrated in vacuo to give 0.280 g yellow solid. 6 mL MeOH was added to the solid and the slurry sonicated for 2 min. The slurry was filtered, and the solid rinsed 1×1 mL MeOH, 1×1 mL diethyl ether, and dried in vacuo to give 6,7-difluoro-N-(5-(3-(2-(methylthio)pyrimidin-4-yl)pyridin-2-yloxy)pyridin-2-yl)-1H-benzo[d]imidazol-2-amine as a light yellow solid. MS m/z=464 $[M+H]^+$. Calc'd for $C_{22}H_{15}F_2N_7OS$: 463.4.

Step 5: give 6,7-difluoro-N-(5-(3-(2-(methylamino) pyrimidin-4-yl)pyridin-2-yloxy)pyridin-2-yl)-1H-benzo[d]imidazol-2-amine To a slurry of 6,7-difluoro-N-(5-(3-(2-(methylthio)pyrimidin-4-yl)pyridin-2-yloxy)pyridin-2-yl)-1H-benzo[d]imidazol-2-amine (0.179 g, 0.39 mmol) in methanol was added oxone(r) (0.65 ml, 1.2 mmol). The reaction was allowed to stir at ambient temperature for 5 h. 1 Equivalent of Oxone was added and the reaction was stirred overnight. 2 mL MeOH and 3 equivalents of Oxone that was finely powdered with a mortar and pestle was added to the reaction, which was stirred for another 24 h. The reaction was concentrated to ½ volume, water was added, and the pH basified with 6 N NaOH at 0° C. The mixture was filtered, and the solid rinsed with water and methanol. The solid was dried in vacuo, and the solid was suspended in 10% MeOH/MC and filtered through a 1 cm plug of silica gel in a frit, eluting with 50 mL 10% MeOH/MC, and concentrated to give a brown solid that was a mixture of 6,7-difluoro-N-(5-(3-(2-(methylsulfinyl)pyrimidin-4-yl) pyridin-2-yloxy)pyridin-2-yl)-1H-benzo[d]imidazol-2-amine and 6,7-difluoro-N-(5-(3-(2-(methylsulfonyl)pyrimidin-4-yl)pyridin-2-yloxy)pyridin-2-yl)-1H-benzo[d] imidazol-2-amine that was used directly in the next reaction.

The mixture of 6,7-difluoro-N-(5-(3-(2-(methylsulfinyl) pyrimidin-4-yl)pyridin-2-yloxy)pyridin-2-yl)-1H-benzo[d] imidazol-2-amine and 6,7-difluoro-N-(5-(3-(2-(methylsulfonyl)pyrimidin-4-yl)pyridin-2-yloxy)pyridin-2-yl)-1H-benzo [d]imidazol-2-amine (0.140 g, 0.28 mmol) in methylamine, 2.0 M solution in THF (2.1 ml, 4.2 mmol) was heated in a sealed tube to 70° C. After 4 h, the reaction was partitioned between EtOAc and 1 N NaOH, and the aqueous suspension was extracted 1×EtOAc, 3× dichloromethane, and the suspension was then filtered and rinsed with methanol. The solid material was combined with the combined organic layers adsorbed onto 2 g silica gel and purified with silica gel chromatography, eluting with 0-75% MC-90/10 MC/MeOH to give a white solid. The solid was sonicated in methanol and filtered, rinsing with $Et_2O$. The resulting material was dried in vacuo to give 6,7-difluoro-N-(5-(3-(2-(methylamino)pyrimidin-4-yl)pyridin-2-yloxy)pyridin-2-yl)-1H-benzo[d]imidazol-2-amine as a white solid. MS m/z=447 $[M+H]^+$. Calc'd for $C_{22}H_{16}F_2N_8O$: 446.4.

The following compounds exemplified in Table I were made using various of the Methods A, B1-B3, C, D, E and F1-F3 described in the examples above.

TABLE I

| Ex. No. | Compound Name | MS (M + H+) | Method |
|---|---|---|---|
| 15 | N-(4-((3-(2-(methylamino)-4-pyrimidinyl)-2-pyridinyl)oxy)-1-naphthalenyl)-1H-benzimidazol-2-amine | 460 | A |
| 16 | N-(4-((3-(2-(methylamino)-4-pyrimidinyl)-2-pyridinyl)oxy)-1-naphthalenyl)-5-(trifluoromethyl)-1H-benzimidazol-2-amine | 528 | A |
| 17 | N-(4-((3-(4-(methylamino)-1,3,5-triazin-2-yl)-2-pyridinyl)oxy)-1-naphthalenyl)-1H-benzimidazol-2-amine | 461 | A |
| 18 | N-(4-((3-(2-(methylamino)-4-pyrimidinyl)-2-pyridinyl)oxy)-1-naphthalenyl)-1,3-benzoxazol-2-amine | 461 | A |
| 19 | N-(4-((3-(2-(methylamino)-4-pyrimidinyl)-2-pyridinyl)oxy)-1-naphthalenyl)-1,3-benzothiazol-2-amine | 477 | A |
| 20 | 5,6-difluoro-N-(4-((3-(2-(methylamino)-4-pyrimidinyl)-2-pyridinyl)oxy)-1-naphthalenyl)-1H-benzimidazol-2-amine | 496 | A |
| 21 | 4-methyl-N-(4-((3-(2-(methylamino)-4-pyrimidinyl)-2-pyridinyl)oxy)-1-naphthalenyl)-1H-benzimidazol-2-amine | 474 | A |
| 22 | N-(4-((3-(2-((2-(4-morpholinyl)ethyl) amino)-4-pyrimidinyl)-2-pyridinyl)oxy)-1-naphthalenyl)-1H-benzimidazol-2-amine | 559 | A |
| 23 | 6-chloro-5-fluoro-N-(4-((3-(2-(methylamino)-4-pyrimidinyl)-2-pyridinyl)oxy)-1-naphthalenyl)-1H-benzimidazol-2-amine | 512 | A |

TABLE I-continued

| Ex. No. | Compound Name | MS (M + H$^+$) | Method |
|---|---|---|---|
| 24 | N-(4-((3-(2-(methylsulfanyl)-4-pyrimidinyl)-2-pyridinyl)oxy)-1-naphthalenyl)-1H-benzimidazol-2-amine | 477 | A |
| 25 | N~1~-(4-(2-((4-(1H-benzimidazol-2-ylamino)-1-naphthalenyl)oxy)-3-pyridinyl)-2-pyrimidinyl)-N~2~,N~2~-dimethyl-1,2-ethanediamine | 517 | F1 |
| 26 | N~1~-(4-(2-((4-(1H-benzimidazol-2-ylamino)-1-naphthalenyl)oxy)-3-pyridinyl)-2-pyrimidinyl)-N~3~,N~3~-dimethyl-1,3-propanediamine | 531 | F1 |
| 27 | N-(4-((3-(2-(methylsulfonyl)-4-pyrimidinyl)-2-pyridinyl)oxy)-1-naphthalenyl)-1H-benzimidazol-2-amine | 509 | F1 |
| 28 | 5,7-difluoro-N-(4-((3-(2-(methylamino)-4-pyrimidinyl)-2-pyridinyl)oxy)-1-naphthalenyl)-1H-benzimidazol-2-amine | 496 | A |
| 29 | N~1~-(4-(2-((4-(1H-benzimidazol-2-ylamino)-1-naphthalenyl)oxy)-3-pyridinyl)-2-pyrimidinyl)-N~4~,N~4~-dimethyl-1,4-butanediamine | 545 | F1 |
| 30 | N-(4-((3-(2-(methylamino)-4-pyrimidinyl)-2-pyridinyl)oxy)-1-naphthalenyl)-5,7-bis(trifluoromethyl)-1H-benzimidazol-2-amine | 596 | A |
| 31 | N-(4-((3-(2-(methylamino)-4-pyrimidinyl)-2-pyridinyl)oxy)-1-naphthalenyl)-3H-imidazo[4,5-b]pyridin-2-amine | 461 | A |
| 32 | N-(4-((3-(2-(methylamino)-4-pyrimidinyl)-2-pyridinyl)oxy)-1-naphthalenyl)-3H-imidazo[4,5-c]pyridin-2-amine | 461 | A |
| 33 | 1-(3-(dimethylamino)propyl)-N-(4-((3-(2-(methylamino)-4-pyrimidinyl)-2-pyridinyl)oxy)-1-naphthalenyl)-1H-benzimidazol-2-amine | 545 | A |
| 34 | 1-(2-(dimethylamino)ethyl)-N-(4-((3-(2-(methylamino)-4-pyrimidinyl)-2-pyridinyl)oxy)-1-naphthalenyl)-1H-benzimidazol-2-amine | 531 | A |
| 35 | N-(4-((3-(2-((3-(1-pyrrolidinyl)propyl) amino)-4-pyrimidinyl)-2-pyridinyl)oxy)-1-naphthalenyl)-1H-benzimidazol-2-amine | 557 | F1 |
| 36 | N-(3-methyl-4-((3-(2-(methylamino)-4-pyrimidinyl)-2-pyridinyl)oxy)-1-naphthalenyl)-1H-benzimidazol-2-amine | 474 | A |
| 37 | N-(3,5-dichloro-4-((3-(2-(methylamino)-4-pyrimidinyl)-2-pyridinyl)oxy)phenyl)-1H-benzimidazol-2-amine | 478 | A |
| 38 | N-1H-benzimidazol-2-yl-8-((3-(2-(methylamino)-4-pyrimidinyl)-2-pyridinyl)oxy)-5-quinolinamine | 461 | A |
| 39 | 4,5-difluoro-N-(4-((3-(2-(methylamino)-4-pyrimidinyl)-2-pyridinyl)oxy)-1-naphthalenyl)-1H-benzimidazol-2-amine | 461 | A |
| 40 | 6,7-difluoro-N-(6-((3-(2-(methylamino)-4-pyrimidinyl)-2-pyridinyl)oxy)-3-pyridinyl)-1H-benzimidazol-2-amine | 447 | A |
| 41 | N-(4-((2-(2-(methylamino)-4-pyrimidinyl)phenyl)oxy)phenyl)-1H-benzimidazol-2-amine | 409 | A |
| 42 | 6,7-difluoro-N-(4-((2-(2-(methylamino)-4-pyrimidinyl)phenyl)oxy)phenyl)-1H-benzimidazol-2-amine | 445 | A |
| 43 | 2-((4-(1H-benzimidazol-2-ylamino) phenyl)oxy)-N-methyl-3,4'-bipyridin-2'-amine | 409 | A |
| 44 | 2-((4-((6,7-difluoro-1H-benzimidazol-2-yl)amino)phenyl)oxy)-N-methyl-3,4'-bipyridin-2'-amine | 445 | A |
| 45 | N-(4-((3-(2-amino-4-pyrimidinyl)-2-pyridinyl)oxy)-3-methyl-1-naphthalenyl)-1H-benzimidazol-2-amine | 460 | A |
| 46 | N-(4-((3-(2-((2-(1-methyl-2-pyrrolidinyl)ethyl)amino)-4-pyrimidinyl)-2-pyridinyl)oxy)-1-naphthalenyl)-1H-benzimidazol-2-amine | 557 | F1 |
| 47 | 5,7-dimethyl-N-(3-methyl-4-((3-(4-pyrimidinyl)-2-pyridinyl)oxy)phenyl)-1,3-benzoxazol-2-amine | 424 | A |
| 48 | 6-methyl-N-(3-methyl-4-((3-(4-pyrimidinyl)-2-pyridinyl)oxy)phenyl)-1,3-benzoxazol-2-amine | 410 | A |
| 49 | 5-methyl-N-(3-methyl-4-((3-(4-pyrimidinyl)-2-pyridinyl)oxy)phenyl)-1,3-benzoxazol-2-amine | 410 | A |
| 50 | 4-methyl-N-(3-methyl-4-((3-(4-pyrimidinyl)-2-pyridinyl)oxy)phenyl)-1,3-benzoxazol-2-amine | 410 | A |
| 51 | N-(4-((3-(2-(((1-ethyl-4-piperidinyl) methyl)amino)-4-pyrimidinyl)-2-pyridinyl)oxy)-1-naphthalenyl)-1H-benzimidazol-2-amine | 571 | F1 |
| 52 | N-(4-((3-(2-((1-methyl-4-piperidinyl) amino)-4-pyrimidinyl)-2-pyridinyl)oxy)-1-naphthalenyl)-1H-benzimidazol-2-amine | 543 | F1 |
| 53 | 4,5-difluoro-N-(4-((3-(1H-pyrazol-4-yl)-2-pyridinyl)oxy)phenyl)-1H-benzimidazol-2-amine | 405 | A |
| 54 | N-(4-((3-(1H-pyrazol-4-yl)-2-pyridinyl) oxy)phenyl)-1H-benzimidazol-2-amine | 369 | A |

TABLE I-continued

| Ex. No. | Compound Name | MS (M + H$^+$) | Method |
|---|---|---|---|
| 55 | N-(4-((3-(2-amino-4-pyrimidinyl)-2-pyridinyl)oxy)phenyl)-4,5-difluoro-1H-benzimidazol-2-amine | 432 | A |
| 56 | N-(6-((3-(2-amino-4-pyrimidinyl)-2-pyridinyl)oxy)-3-pyridinyl)-6,7-difluoro-1H-benzimidazol-2-amine | 433 | A |
| 57 | N-(4-((3-(2-(methylamino)-4-pyrimidinyl)-2-pyridinyl)oxy)phenyl)-1,3-benzoxazol-2-amine | 411 | A |
| 58 | N-(4-((3-(2-(methylamino)-4-pyrimidinyl)-2-pyridinyl)oxy)phenyl)-1H-benzimidazol-2-amine | 410 | A |
| 59 | N-(3-methyl-4-((3-(2-(methylamino)-4-pyrimidinyl)-2-pyridinyl)oxy)phenyl)-1,3-benzoxazol-2-amine | 425 | A |
| 60 | N-(3-methyl-4-((3-(2-(methylamino)-4-pyrimidinyl)-2-pyridinyl)oxy)phenyl)-1H-benzimidazol-2-amine | 424 | A |
| 61 | N-(4-((3-(2-(methylamino)-4-pyrimidinyl)-2-pyridinyl)oxy)phenyl)-1,3-benzothiazol-2-amine | 427 | A |
| 62 | 5-methyl-N-(4-((3-(2-(methylamino)-4-pyrimidinyl)-2-pyridinyl)oxy)phenyl)-1H-benzimidazol-2-amine | 424 | A |
| 63 | N-(4-((3-(2-(methylamino)-4-pyrimidinyl)-2-pyridinyl)oxy)phenyl)-5-(trifluoromethyl)-1H-benzimidazol-2-amine | 478 | A |
| 64 | 5-methyl-N-(3-methyl-4-((3-(2-(methylamino)-4-pyrimidinyl)-2-pyridinyl)oxy)phenyl)-1H-benzimidazol-2-amine | 438 | A |
| 65 | N-(3-methyl-4-((3-(2-(methylamino)-4-pyrimidinyl)-2-pyridinyl)oxy)phenyl)-5-(trifluoromethyl)-1H-benzimidazol-2-amine | 492 | A |
| 66 | 1-methyl-N-(3-methyl-4-((3-(2-(methylamino)-4-pyrimidinyl)-2-pyridinyl)oxy)phenyl)-1H-benzimidazol-2-amine | 438 | A |
| 67 | 1-methyl-N-(4-((3-(2-(methylamino)-4-pyrimidinyl)-2-pyridinyl)oxy)phenyl)-1H-benzimidazol-2-amine | 424 | A |
| 68 | 1-methyl-N-(4-((3-(2-(methylamino)-4-pyrimidinyl)-2-pyridinyl)oxy)phenyl)-5-(trifluoromethyl)-1H-benzimidazol-2-amine | 492 | A |
| 69 | 5,6-difluoro-N-(4-((3-(2-(methylamino)-4-pyrimidinyl)-2-pyridinyl)oxy)phenyl)-1H-benzimidazol-2-amine | 446 | A |
| 70 | 5-(1,1-dimethylethyl)-N-(4-((3-(2-(methylamino)-4-pyrimidinyl)-2-pyridinyl)oxy)phenyl)-1H-benzimidazol-2-amine | 446 | A |
| 71 | 6-chloro-5-fluoro-N-(4-((3-(2-(methylamino)-4-pyrimidinyl)-2-pyridinyl)oxy)phenyl)-1H-benzimidazol-2-amine | 463 | A |
| 72 | 4-methyl-N-(4-((3-(2-(methylamino)-4-pyrimidinyl)-2-pyridinyl)oxy)phenyl)-1H-benzimidazol-2-amine | 424 | A |
| 73 | 5-fluoro-N-(4-((3-(2-(methylamino)-4-pyrimidinyl)-2-pyridinyl)oxy)phenyl)-1H-benzimidazol-2-amine | 428 | A |
| 74 | 4-methyl-N-(3-methyl-4-((3-(2-(methylamino)-4-pyrimidinyl)-2-pyridinyl)oxy)phenyl)-1H-benzimidazol-2-amine | 438 | A |
| 75 | 5-fluoro-N-(3-methyl-4-((3-(2-(methylamino)-4-pyrimidinyl)-2-pyridinyl)oxy)phenyl)-1H-benzimidazol-2-amine | 442 | A |
| 76 | 5,6-difluoro-N-(3-methyl-4-((3-(2-(methylamino)-4-pyrimidinyl)-2-pyridinyl)oxy)phenyl)-1H-benzimidazol-2-amine | 460 | A |
| 77 | 6-chloro-5-fluoro-N-(3-methyl-4-((3-(2-(methylamino)-4-pyrimidinyl)-2-pyridinyl)oxy)phenyl)-1H-benzimidazol-2-amine | 476 | A |
| 78 | N-(2-methyl-4-((3-(2-(methylamino)-4-pyrimidinyl)-2-pyridinyl)oxy)phenyl)-1H-benzimidazol-2-amine | 424 | A |
| 79 | N-(2,3-dimethyl-4-((3-(2-(methylamino)-4-pyrimidinyl)-2-pyridinyl)oxy)phenyl)-1H-benzimidazol-2-amine | 438 | A |
| 80 | 5,6-dimethyl-N-(4-(3-(2-(methylamino)pyrimidin-4-yl)pyridin-2-yloxy)phenyl)-1H-benzo[d]imidazol-2-amine | 438 | A |
| 81 | 4,6-difluoro-N-(4-((3-(2-(methylamino)-4-pyrimidinyl)-2-pyridinyl)oxy)phenyl)-1H-benzimidazol-2-amine | 446 | A |
| 82 | 4,5-dimethyl-N-(4-((3-(2-(methylamino)-4-pyrimidinyl)-2-pyridinyl)oxy)phenyl)-1H-benzimidazol-2-amine | 438 | A |
| 83 | 5-fluoro-N-(4-((3-(2-((3-(4-morpholinyl)propyl)amino)-4-pyrimidinyl)-2-pyridinyl)oxy)phenyl)-1H-benzimidazol-2-amine | 541 | A |
| 84 | 5,6-dichloro-N-(4-((3-(2-(methylamino)-4-pyrimidinyl)-2-pyridinyl)oxy)phenyl)-1H-benzimidazol-2-amine | 478 | A |
| 85 | N-(4-((3-(2-(methylamino)-4-pyrimidinyl)-2-pyridinyl)oxy)phenyl)-4,6-bis(trifluoromethyl)-1H-benzimidazol-2-amine | 546 | A |

TABLE I-continued

| Ex. No. | Compound Name | MS (M + H⁺) | Method |
|---|---|---|---|
| 86 | 5-chloro-6-methyl-N-(4-((3-(2-(methylamino)-4-pyrimidinyl)-2-pyridinyl)oxy)phenyl)-1H-benzimidazol-2-amine | 458 | A |
| 87 | 5-fluoro-N-(4-((3-(2-((4-(4-methyl-1-piperazinyl)phenyl)amino)-4-pyrimidinyl)-2-pyridinyl)oxy)phenyl)-1H-benzimidazol-2-amine | 588 | A |
| 88 | N-(4-((3-(2-(methylamino)-4-pyrimidinyl)-2-pyridinyl)oxy)phenyl)-5-(4-methyl-1-piperazinyl)-1H-benzimidazol-2-amine | 508 | A |
| 89 | N'-(4-(2-((4-((5,6-difluoro-1H-benzimidazol-2-yl)amino)phenyl)oxy)-3-pyridinyl)-2-pyrimidinyl)-N,N-dimethyl-1,3-propanediamine | 517 | A |
| 90 | 4,5-difluoro-N-(4-((3-(2-(methylamino)-4-pyrimidinyl)-2-pyridinyl)oxy)phenyl)-1H-benzimidazol-2-amine | 446 | A |
| 91 | N-(4-((3-(2-((3-(1-piperidinyl)propyl)amino)-4-pyrimidinyl)-2-pyridinyl)oxy)-1-naphthalenyl)-1H-benzimidazol-2-amine | 571 | F1 |
| 92 | N'-(4-(2-((4-(1H-benzimidazol-2-ylamino)-1-naphthalenyl)oxy)-3-pyridinyl)-2-pyrimidinyl)-N,N,2,2-tetramethyl-1,3-propanediamine | 559 | F1 |
| 93 | 5,6-difluoro-N-(4-((3-(1H-pyrrolo[2,3-b]pyridin-4-yl)-2-pyridinyl)oxy) phenyl)-1H-benzimidazol-2-amine | 455 | A |
| 94 | N-(4-((3-(2-((3-(1H-1,2,3-triazol-1-yl)propyl)amino)-4-pyrimidinyl)-2-pyridinyl)oxy)-1-naphthalenyl)-1H-benzimidazol-2-amine | 555 | F1 |
| 95 | 5,6-difluoro-N-(4-((3-(2-((3-(4-thiomorpholinyl)propyl)amino)-4-pyrimidinyl)-2-pyridinyl)oxy)phenyl)-1H-benzimidazol-2-amine | 575 | F1 |
| 96 | N'-(4-(2-((4-((5,6-difluoro-1H-benzimidazol-2-yl)amino)phenyl)oxy)-3-pyridinyl)-2-pyrimidinyl)-N,N-dimethyl-1,4-butanediamine | 531 | F1 |
| 97 | 2,2'-((3-((4-(2-((4-((5,6-difluoro-1H-benzimidazol-2-yl)amino)phenyl)oxy)-3-pyridinyl)-2-pyrimidinyl)amino)propyl) imino)diethanol | 577 | F1 |
| 98 | N'-(4-(2-((4-((5,6-difluoro-1H-benzimidazol-2-yl)amino)phenyl)oxy)-3-pyridinyl)-2-pyrimidinyl)-N,N-dimethyl-1,5-pentanediamine | 545 | F1 |
| 99 | N'-(4-(2-((4-((5,6-difluoro-1H-benzimidazol-2-yl)amino)phenyl)oxy)-3-pyridinyl)-2-pyrimidinyl)-N,N-dimethyl-1,6-hexanediamine | 559 | F1 |
| 100 | 5,6-difluoro-N-(4-((3-(2-((3-(4-morpholinyl)propyl)amino)-4-pyrimidinyl)-2-pyridinyl)oxy)phenyl)-1H-benzimidazol-2-amine | 559 | F1 |
| 101 | 4,5,6-trifluoro-N-(4-(3-(2-(methylamino)pyrimidin-4-yl)pyridin-2-yloxy)phenyl)-1H-benzo[d]imidazol-2-amine | 464 | F1 |
| 102 | N-(4-(3-(2-(methylamino)pyrimidin-4-yl)pyridin-2-yloxy)phenyl)-1H-thieno[3,4-d]imidazol-2-amine | 416 | F1 |
| 103 | N-(4-((3-(1H-pyrrolo[2,3-b]pyridin-4-yl)-2-pyridinyl)oxy)phenyl)-1H-benzimidazol-2-amine | 419 | F1 |
| 104 | N-(4-((3-(2-(methylamino)-4-pyrimidinyl)-2-pyridinyl)thio)phenyl)-1H-benzimidazol-2-amine | 426 | F1 |
| 105 | 4,5-difluoro-N-(4-((3-(1H-pyrrolo[2,3-b]pyridin-4-yl)-2-pyridinyl)oxy)phenyl)-1H-benzimidazol-2-amine | 455 | F1 |
| 106 | 4,5-difluoro-N-(4-((3-(2-(methylamino)-4-pyrimidinyl)-2-pyridinyl)thio)phenyl)-1H-benzimidazol-2-amine | 462 | F1 |
| 107 | 4,5-difluoro-N-(4-((3-(2-((4-(4-methyl-1-piperazinyl)phenyl)amino)-4-pyrimidinyl)-2-pyridinyl)oxy)phenyl)-1H-benzimidazol-2-amine | 606 | F1 |
| 108 | 4,5-difluoro-N-(4-((3-(2-(methylamino)-4-pyrimidinyl)-2-pyridinyl)oxy)-3-(methyloxy)phenyl)-1H-benzimidazol-2-amine | 476 | F1 |
| 109 | N-(4-((3-(2-(methylamino)-4-pyrimidinyl)-2-pyridinyl)oxy)-3-(methyloxy)phenyl)-1H-benzimidazol-2-amine | 440 | F1 |
| 110 | 4,5-difluoro-N-(3-methyl-4-((3-(2-(methylamino)-4-pyrimidinyl)-2-pyridinyl)oxy)phenyl)-1H-benzimidazol-2-amine | 460 | F1 |
| 111 | 4,5,6,7-tetrafluoro-N-(4-((3-(2-(methylamino)-4-pyrimidinyl)-2-pyridinyl)oxy)phenyl)-1H-benzimidazol-2-amine | 482 | F1 |
| 112 | 4,5-difluoro-N-(2-fluoro-4-((3-(2-(methylamino)-4-pyrimidinyl)-2-pyridinyl)oxy)phenyl)-1H-benzimidazol-2-amine | 464 | F1 |
| 113 | N-(4-((3-(2-(methylamino)-4-pyrimidinyl)-2-pyridinyl)oxy)phenyl)-1-phenyl-1H-benzimidazol-2-amine | 486 | F1 |

TABLE I-continued

| Ex. No. | Compound Name | MS (M + H⁺) | Method |
|---|---|---|---|
| 114 | N-(3-chloro-4-((3-(2-(methylamino)-4-pyrimidinyl)-2-pyridinyl)oxy)phenyl)-4,5-difluoro-1H-benzimidazol-2-amine | 480 | F1 |
| 115 | 4-(2-((4-((1-methyl-4-phenyl-1H-imidazol-2-yl)amino)phenyl)oxy)-3-pyridinyl)-2-pyrimidinamine | 436 | E |
| 116 | N-(4-((3-(2-(methylamino)-4-pyrimidinyl)-2-pyridinyl)oxy)-1-naphthalenyl)-1H-benzimidazol-2-amine | 460 | A |
| 117 | N-(4-((3-(2-(methylamino)-4-pyrimidinyl)-2-pyridinyl)oxy)-1-naphthalenyl)-5-(trifluoromethyl)-1H-benzimidazol-2-amine | 528 | A |
| 118 | N-(4-((3-(4-(methylamino)-1,3,5-triazin-2-yl)-2-pyridinyl)oxy)-1-naphthalenyl)-1H-benzimidazol-2-amine | 461 | A |
| 119 | N-(4-((3-(2-(methylamino)-4-pyrimidinyl)-2-pyridinyl)oxy)-1-naphthalenyl)-1,3-benzoxazol-2-amine | 461 | A |
| 120 | N-(4-((3-(2-(methylamino)-4-pyrimidinyl)-2-pyridinyl)oxy)-1-naphthalenyl)-1,3-benzothiazol-2-amine | 477 | A |
| 121 | 5,6-difluoro-N-(4-((3-(2-(methylamino)-4-pyrimidinyl)-2-pyridinyl)oxy)-1-naphthalenyl)-1H-benzimidazol-2-amine | 496 | A |
| 122 | 4-methyl-N-(4-((3-(2-(methylamino)-4-pyrimidinyl)-2-pyridinyl)oxy)-1-naphthalenyl)-1H-benzimidazol-2-amine | 474 | A |
| 123 | N-(4-((3-(2-((2-(4-morpholinyl)ethyl)amino)-4-pyrimidinyl)-2-pyridinyl)oxy)-1-naphthalenyl)-1H-benzimidazol-2-amine | 559 | A |
| 124 | 6-chloro-5-fluoro-N-(4-((3-(2-(methylamino)-4-pyrimidinyl)-2-pyridinyl)oxy)-1-naphthalenyl)-1H-benzimidazol-2-amine | 513 | A |
| 125 | N-(4-((3-(2-(methylsulfanyl)-4-pyrimidinyl)-2-pyridinyl)oxy)-1-naphthalenyl)-1H-benzimidazol-2-amine | 477 | A |

While the examples described above provide processes for synthesizing compounds of Formulas I-III, other methods may be utilized to prepare such compounds. In the procedures described herein, the steps may be performed in an alternate order and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Those of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Synthetic procedures may also be carried out where functional groups of starting compounds, which are not intended to take part in the reaction, may be present in unprotected form without the added step of protecting that group by, for example, one or more of the protecting groups mentioned above or taught in the references above.

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of the invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

These detailed descriptions fall within the scope, and serve to exemplify, the above-described General Synthetic Procedures which form part of the invention. These detailed descriptions are presented for illustrative purposes only and are not intended as a restriction on the scope of the invention.

Biological Evaluation

Although the pharmacological properties of the compounds of the invention (Formulas I-III) vary with structural change, in general, activity possessed by compounds of Formulas I-III may be demonstrated both in vitro as well as in vivo. Particularly, the pharmacological properties of the compounds of this invention may be confirmed by a number of pharmacological in vitro and/or in vivo assays. The following exemplified pharmacological assays have been carried out with the compounds according to the invention. Briefly, representative compounds of the invention were found to inhibit the activity of the Tie-2 receptor kinase and Aurora kinase, selectively or non-selectively, at doses less than 25 μM. This activity demonstrates the utility of the compounds of the invention as protein kinase inhibitors and in the prophylaxis and treatment of oncological conditions, cell proliferative disorders, cancer, and the like, as described herein.

The following assays can be employed to determine the degree of activity of a compound as a protein kinase inhibitor.

Tie-2-Homogenous Time Resolved Fluorescent (HTRF) Kinase Assay $IC_{50}$'s for the inhibition of the Tie-2 kinase enzyme for individual compounds were measured using an HTRF assay, utilizing the following procedure:

In a 96-well plate (available from Costar Co.) was placed 1 uL of each test and standard compound per well in 100% DMSO having a 25 uM final compound concentration (3-fold, 10 point dilution). To each well was added 20 uL of a reaction mix formed from Tie-2 (4.0 uL; of a 10 mM stock solution available from Gibco), 0.05% BSA (0.1 uL; from a 10% stock solution available from Sigma-Aldrich Co.), 0.002 mM of BLC HER-2 KKK (Biotinylated Long chain peptide; 0.04 uL; from a 0.002 mM stock solution), 0.01 mM concentration of ATP (0.02 uL; commercially available from Sigma-Aldrich Co.) and the remaining solution was water (15.84 uL) to make to a total volume of 20 uL/well.

The reaction was initiated in each well by adding 20 uL per well of an enzyme preparation consisting of a 50 mM concentration of Hepes (1.0 uL; from a 1000 mM stock solution commercially available from Gibco Co.), 0.05% concentration of BSA (0.1 uL), 4 mM of DTT (0.08 uL; from a 1000 mM stock solution available from Sigma-Aldrich Co.), a $2.4\times10^{-7}$ concentration of Tie-2 (0.02 uL, from a 4 mM concentration stock), with the remaining volume being water (18.8 uL) to dilute the enzyme preparation to a total volume of 20 uL. The plate was incubated for about 90 minutes at RT. After incubation, a 160 uL of a filtered detection mixture, prepared from 0.001 mg/ml of SA-APC (0.0765 uL; available as a 2.09 mg/ml stock solution from Gibco), 0.03125 nM concentration of Eu-Ab (0.1597 uL; available in a 31.3 nM stock solution from Gibco), with the remaining volume being Detection buffer (159.73 uL), was added to each well to stop the reaction therein. The plate was then allowed to equilibrate for about 3 hr and read on a Ruby Star fluorescent reader (available from BMG Technologies, Inc.) using a 4 parameter fit using activity base to calculate the corresponding $IC_{50}$'s for the test and standard compounds in each well. Examples 4-6, 8-46, 51-61, 63-65, 68-103 and 105-115 were found to have $IC_{50}$'s for the inhibition of Tie-2 as measured by the HTRF assay of less than or equal to 5 uM.

The compounds of the invention also were found to have inhibitory activity with respect to Aurora kinase enzymes. The exemplary assays described as follows were used to make such determination.

Aurora Kinase HTRF Assays

AuroraA-TPX2-Homogeneous Time Resolved Fluorescent (HTRF) Kinase Assay:

The AuroraA HTRF assay begins with AuroraA in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The AuroraA HTRF assay comprises 1 μL of compound in 100% DMSO, 20 μL of ATP and biotinylated PLK, and 20 μL of AuroraA-TPX2 KD GST for a final volume of 41 μL. The final concentration of PLK is about 1 μM. The final concentration of ATP is about 1 μM (Km(app)=1 μM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

The following exemplary compounds 5-7, 10-12, 15-26, 28-38, 46, 48, 51-54, 57-106 and 115, exhibited $IC_{50}$ activity of less than or equal to 5 μM in the Aurora kinase A HTRF assay.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quenched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 μL of compound in 100% DMSO, 20 μL of ATP and biotinylated Histone H3, and 20 μL of AuroraB FL His for a final volume of 41 μL. The final concentration of Histone H3 is 0.1 μM. The final concentration of ATP is 23 μM (Km(app)=23 μM+/−2.6) and the final concentration of AuroraB is 400 pM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-HisH3) at a final conc of 0.064 nM.

The assay plate is read in either a Discovery or a RubyStar. The eu-anti-HisH3 is excited at 320 nm and emits at 615 nm to excite the SA-APC which in turn emits at 655 nm. The ratio of SA-APC at 655 nm (excited due to close proximity to the Eu-anti-HisH3 because of phosphorylation of the peptide) to free Eu-anti-HisH3 at 615 nm will give substrate phosphorylation.

The following exemplary compounds 4-6, 8-46 and 51-115, exhibited $IC_{50}$ activity of less than or equal to 5 μM in the Aurora kinase B HTRF assay.

Indications

The compounds of the invention have kinase modulatory activity for both Tie-2 and Aurora kinase. In one embodiment of the invention, there is provided a method of modulating tie-2 or Aurora kinase in a subject, the method comprising administering to the subject an effective dosage amount of a compound of a compound of Formulas I-III.

Accordingly, compounds of the invention are useful for, but not limited to, the prevention or treatment of angiogenesis and cell-cycling and cell proliferation-related diseases. The compounds may be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds are useful for the treatment of neoplasia selected from lung cancer, colon cancer and breast cancer.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the invention are also useful in the treatment of diabetic conditions such as diabetic retinopathy and microangiopathy.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions comprising the active compounds of Formulas I-III in association with one or more non-toxic, pharmaceutically-acceptable carriers and/or diluents and/or adjuvants (collectively referred to herein as "carrier" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid, which can be made using known, conventional methods. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

The foregoing is merely illustrative of the invention and is not intended to limit the invention to the disclosed compounds. Variations and changes, which are obvious to one skilled in the art, are intended to be within the scope and nature of the invention, which are defined in the appended claims.

All mentioned references, patents, applications and publications, are hereby incorporated by reference in their entirety, as if here written.

What is claimed is:

1. A compound of Formula I:

I

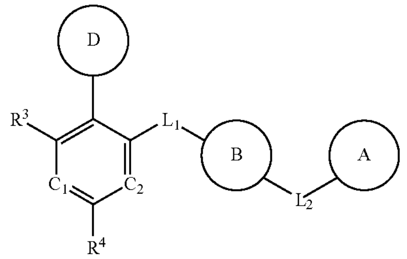

or a stereoisomer or pharmaceutically acceptable salt thereof, wherein

A is a ring selected from

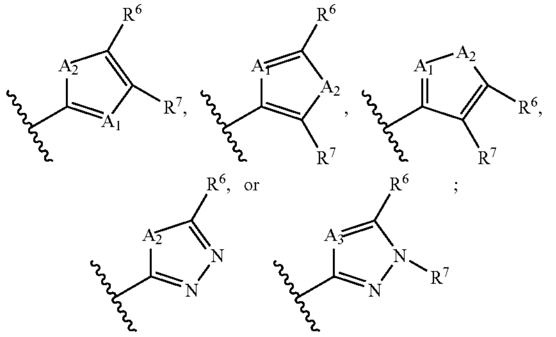

wherein each of $A^1$ and $A^3$ independently, is N or $CR^8$ and $A^2$ is $NR^9$, O or S;

B is a fully unsaturated 5-6 membered first monocyclic ring, said first ring (1) formed of carbon atoms optionally including 1-3 heteroatoms selected from O, N, or S, (2) optionally fused to a partially or fully saturated or fully unsaturated 5-6 membered second monocyclic ring formed of carbon atoms optionally including 1-3 heteroatoms selected from O, N, or S, and (3) wherein 0, 1, 2 or 3 atoms of each of said first and second ring is optionally substituted independently with 1-4 substituents of $R^5$;

$C^1$ is N or $CR^{10}$;

$C^2$ is N or CH, provided that (1) when $C^1$ is N then $C^2$ is CH or (2) when $C^1$ is $CR^{10}$ then $C^2$ is N;

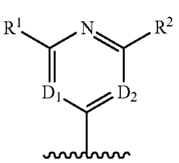 or 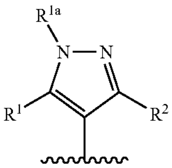

D is wherein $D^1$ is N or $CR^{11}$;

$D^2$ is N or $CR^{12}$;

$R^1$ is H, $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$, wherein n is 0, 1, 2, 3 or 4;

$R^{1a}$ is H, CN or $C_{1-10}$alkyl;

alternatively $R^1$ taken together with either of $R^{11}$ and $R^{1a}$ and the carbon or nitrogen atoms to which they are attached form a partially or fully unsaturated 5- or 6-membered ring of carbon atoms optionally including 1-3 heteroatoms selected from O, N and S, and the ring optionally substituted independently with 1-3 substituents of $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$; and $R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

$L^1$ is $NR^3$, O, S, C(O), S(O), $SO_2$ or $CR^3R^3$;

$L^2$ is $NR^3$, O, S, C(O), S(O), $SO_2$ or $CR^3R^3$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-3 substituents of $R^{13}$, $R^{14}$ or $R^{15}$;

each $R^5$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

each of $R^6$, $R^7$ and $R^8$, independently, is $R^{13}$, $R^{14}$ or $R^{15}$;

alternatively, $R^6$ and $R^7$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

$R^9$ is $R^{15}$;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$; and $R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

provided that (1) no more than one of $D^1$ and $D^2$ is N, and (2) each of $L^1$ and $L^2$ is, independently, bound to the first ring of B.

2. The compound of claim 1, wherein $D^1$ is N, $D^2$ is $CR^{12}$.

3. The compound of claim 1, wherein $D^2$ is N and $D^1$ is $CR^{11}$.

4. The compound of claim 1, wherein $C^1$ is $CR^{19}$;

$C^2$ is N; and $R^2$ is H, halo, $NO_2$, CN, $C_{1-10}$alkyl or $C_{1-10}$alkoxyl.

5. The compound of claim 1, wherein $L^1$ is $NR^{15}$, O, S, S(O) or $SO_2$; and $R^2$ is H, halo, $NO_2$, CN, $C_{1-10}$alkyl or $C_{1-10}$alkoxyl.

6. The compound of claim 1, wherein $L^1$ is $NR^{15}$, O or S;

$L^2$ is $NR^{15}$ wherein $R^{15}$ is H or $C_{1-3}$alkyl;

$R^2$ is H, halo, $NO_2$, CN, $C_{1-10}$alkyl or $C_{1-10}$alkoxyl;

each of $R^3$, $R^4$ and $R^9$, independently, is H; and $C^1$ is $CR^{10}$.

7. The compound of claim 1, wherein the first monocyclic ring of B is phenyl, pyridyl, pyrimidinyl, pyridazinyl, pyrazinyl, triazinyl, thiophenyl, furyl, pyrrolyl, pyrazolyl, imidazolyl, triazolyl, tetrazolyl, thiazolyl, thiadiazolyl, oxazolyl, oxadiazolyl, isoxazolyl, or isothiazolyl; and where the first monocyclic ring of B is a fully unsaturated 6-membered ring, then $L^1$ and $L^2$, together, are para to one another on said first monocyclic ring of B.

8. The compound of claim 7, wherein $R^6$ and $R^7$ taken together with the carbon atoms to which they are attached form a partially or fully unsaturated 5- or 6-membered ring of carbon atoms optionally including 1-3 nitrogen atoms, and the ring optionally substituted independently with 1-4 substituents of $R^{13}$, $R^{14}$ or $R^{15}$.

9. The compound of claim 8, wherein A is

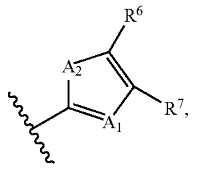

wherein $A^1$ is N and $A^2$ is NH, O or S.

10. The compound of claim 9, wherein $R^6$ and $R^7$ taken together with the carbon atoms to which they are attached form a phenyl ring optionally substituted independently with 1-3 substituents of $R^{15}$.

11. The compound of claim 1, wherein A is

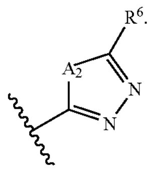

12. The compound of claim 1, wherein A is

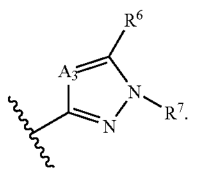

13. A compound of Formula II:

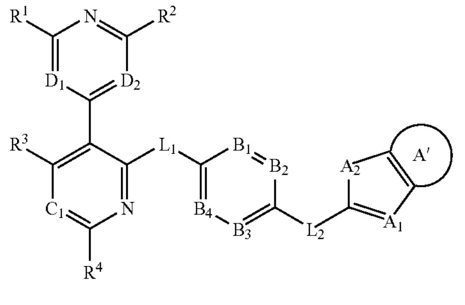

II or a stereoisomer or pharmaceutically acceptable salt thereof, wherein $A^1$ is N or $CR^8$;

$A^2$ is $NR^9$, O or S;

A' is a fused ring selected from phenyl, pyridine, pyrimidine and pyridazine, each of which is optionally substituted independently with 1-3 substituents of $R^{13}$, $R^{14}$ or $R^{15}$;

each of $B^1$, $B^2$, $B^3$ and $B^4$, independently, is N or $CR^5$, provided that no more than two of $B^1$, $B^2$, $B^3$ and $B^4$ is N;

alternatively, each of $B^1$ and $B^2$, independently, is $CR^5$, wherein both $R^5$ groups taken together with the carbon atoms to which they are attached form a 5- or 6-membered ring of carbon atoms, said ring optionally including 1-3 heteroatoms selected from N, O or S, and optionally substituted with 1-4 substituents of $R^{13}$, $R^{14}$ or $R^{15}$;

$C^1$ is N or $CR^{10}$;

$D^1$ is N or $CR^{11}$;

$D^2$ is N or $CR^{12}$;

$L^1$ is $NR^3$, O, S or $CR^3R^3$;

$L^2$ is $NR^3$, O, S or $CR^3R^3$;

$R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$, wherein n is 0, 1, 2, 3 or 4;

alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-4 substituents of $R^{15}$, $SR^{14}$, $OR^{14}$, $SR^{15}$, $OR^{15}$, $OC(O)R^{15}$, $COOR^{15}$, $C(O)R^{15}$, $C(O)NR^{15}R^{15}$, $NR^{14}R^{15}$ or $NR^{15}R^{15}$;

$R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}C(O)C(O)NR^{14}R^{15}$, $NR^{15}C(O)C(O)NR^{15}R^{15}$ or $R^{15}$;

$R^8$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^9$ is H, halo, haloalkyl, haloalkoxyl, oxo, CN, OH, SH, $NO_2$, $NH_2$, acetyl, $C_{1-10}$-alkyl, $C_{1-10}$-alkoxyl, $C_{2-10}$-alkenyl, $C_{2-10}$-alkynyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{1-10}$-alkoxyl, $C_{2-10}$-alkenyl, $C_{2-10}$-alkynyl, and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$; and $R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

provided that no more than one of $D^1$ and $D^2$ is N.

14. The compound of claim 13, wherein $A^1$ is N;

$A^2$ is $NR^9$, O or S;

each of $B^1$, $B^2$, $B^3$ and $B^4$, independently, is $CR^5$;

$C^1$ is $CR^{10}$;

$D^1$ is N or $CR^{11}$;

$D^2$ is N or $CR^{12}$;

$L^1$ is NH, O or S;

$L^2$ is NH;

$R^1$ is H, halo, haloalkyl, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl, $NHR^{14}$, $NHR^{15}$, $OR^{15}$, $SR^{15}$ or $CH_2R^{15}$;

$R^2$ is H, halo, $NO_2$, CN, $C_{1-10}$alkyl or $C_{1-10}$alkoxyl;

each of $R^3$ and $R^4$, independently, is $SR^{15}$, $OR^{15}$, $NR^{14}R^{15}$, $NR^{15}R^{15}$, $C(O)R^{14}$, $C(O)R^{15}$ or $R^{15}$;

each $R^5$ is, independently, is $SR^{15}$, $OR^{15}$, $NR^{15}R^{15}$, $C(O)R^{15}$, $C(O)NR^{15}R^{15}$, $NR^{15}C(O)R^{15}$, $NR^{15}C(O)NR^{15}R^{15}$, $NR^{15}(COOR^{15})$, $S(O)_2R^{15}$, $S(O)_2NR^{15}R^{15}$, $NR^{15}S(O)_2NR^{15}R^{15}$, $NR^{15}S(O)_2R^{15}$, $NR^{15}C(O)C(O)NR^{14}R^{15}$ or $R^{15}$; and $R^8$ is $SR^{15}$, $OR^{15}$, $NR^{15}R^{15}$, $C(O)R^{15}$ or $R^{15}$;

$R^9$ is H, CN, acetyl or $C_{1-10}$-alkyl; and each of $R^{10}$, $R^{11}$ and $R^{12}$, independently, is $SR^{15}$, $OR^{15}$, $NR^{15}R^{15}$, $C(O)R^{14}$, $C(O)R^{15}$ or $R^{15}$;

provided that no more than one of $D^1$ and $D^2$ is N.

15. The compound of claim 13 wherein, $R^1$ is $NR^{14}R^{15}$, $NR^{15}R^{15}$, $(CHR^{15})_nR^{14}$, $(CHR^{15})_nR^{15}$ or $R^{15}$; alternatively $R^1$ and $R^{11}$ taken together with the carbon atoms to which they are attached form a partially or fully unsaturated 5- or 6-membered ring of carbon atoms optionally including 1-3 heteroatoms selected from O, N and S, and the ring optionally substituted independently with 1-4 substituents of $R^{15}$;

$R^2$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

each of $R^3$ and $R^4$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl;

each $R^5$ is, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino or diisopropylamino;

$R^8$ is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino or diisopropylamino;

$R^9$ is H or $C_{1-10}$-alkyl; and each of $R^{10}$, $R^{11}$ and $R^{12}$, independently, is H, halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino or diisopropylamino.

16. A compound of Formula III:

III

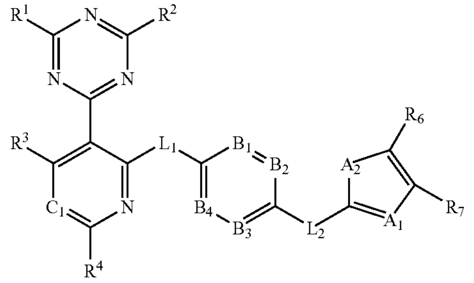

or a stereoisomer or pharmaceutically acceptable salt thereof, wherein $A^1$ is N or $CR^8$;

$A^2$ is $NR^9$, O or S;

each of $B^1$, $B^2$, $B^3$ and $B^4$, independently, is N or $CR^5$, provided that no more than two of $B^1$, $B^2$, $B^3$ and $B^4$ is N;

$C^1$ is $CR^{10}$;

$L^1$ is O, S, C(O), S(O), $SO_2$ or $CR^3R^3$;

$L^2$ is $NR^3$, O, S or $CR^3R^3$;

$R^1$ is $OR^{14}$, $SR^{14}$, $OR^{15}$, $SR^{15}$, $NR^{14}R^{15}$, $NR^{15}R^{15}$, $(CHR^{15})_nR^{14}$, $(CHR^{15})_nR^{15}$ or $R^{15}$;

$R^2$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{14}R^{15}$, $NR^{15}S(O)_2NR^{15}R^{15}$, $NR^{15}S(O)_2R^{14}$, $NR^{15}S(O)_2R^{15}$ or $R^{15}$;

each of $R^3$ and $R^4$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

alternatively, either of $R^3$ or $R^4$, independently, taken together with $R^{10}$ and the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

each $R^5$ is, independently, is $SR^{14}$, $OR^{14}$, $SR^{15}$, $OR^{15}$, $NR^{14}R^{15}$, $NR^{15}R^{15}$, $C(O)R^{14}$, $NR^{15}C(O)R^{15}$, $COOR^{15}$, $OC(O)R^{15}$, $C(O)C(O)R^{15}$, $C(O)NR^{14}R^{15}$, $C(O)NR^{15}R^{15}$, $NR^{15}C(O)R^{14}$, $NR^{15}C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{15})$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2NR^{15}R^{15}$, $NR^{15}S(O)_2R^{14}$, $NR^{15}S(O)_2R^{15}$, $NR^{15}S(O)_2NR^{14}R^{15}$, $NR^{15}$, $C(O)C(O)NR^{14}R^{15}$, $NR^{15}C(O)C(O)NR^{15}R^{15}$ or $R^{15}$;

each of $R^6$, $R^7$ and $R^8$, independently, is $R^{13}$, $R^{14}$ or $R^{15}$;

alternatively, $R^6$ and $R^7$ taken together with the carbon atoms to which they are attached form a partially or fully unsaturated 5- or 6-membered ring of carbon atoms optionally including 1-3 heteroatoms selected from O, N, or S, and the ring optionally substituted independently with 1-4 substituents of $R^{13}$, $R^{14}$ or $R^{15}$;

$R^9$ is $R^{15}$;

each of $R^{10}$, $R^{11}$ and $R^{12}$, independently, is $SR^{14}$, $OR^{14}$, $SR^{15}$, $OR^{15}$, $NR^{14}R^{15}$, $NR^{15}R^{15}$, $C(O)R^{14}$, $C(O)R^{15}$ or $R^{15}$;

$R^{13}$ is $SR^{14}$, $OR^{14}$, $SR^{15}$, $OR^{15}$, $NR^{14}R^{15}$, $NR^{15}R^{15}$, $C(O)R^{14}$, $C(O)R^{15}$, $OC(O)R^{14}$, $OC(O)R^{15}$, $COOR^{14}$, $COOR^{15}$, $C(O)NR^{14}R^{15}$, $C(O)NR^{15}R^{15}$, $NR^{15}C(O)R^{14}$, $NR^{15}C(O)R^{15}$, $C(O)C(O)R^{15}$, $NR^{15}C(O)NR^{14}R^{15}$, $NR^{15}C(O)NR^{15}R^{15}$, $NR^{15}C(O)C(O)R^{15}$, $NR^{15}(COOR^{14})$, $NR^{15}(COOR^{15})$, $NR^{15}C(O)C(O)NR^{14}R^{15}$, $NR^{15}C(O)C(O)NR^{15}R^{15}$, $S(O)_2R^{14}$, $S(O)_2R^{15}$, $S(O)_2NR^{14}R^{15}$, $S(O)_2NR^{15}R^{15}$, $NR^{15}S(O)_2R^{14}$, $NR^{15}S(O)_2R^{15}$, $NR^{15}S(O)_2NR^{14}R^{15}$ or $NR^{15}S(O)_2NR^{15}R^{15}$;

$R^{14}$ is a partially or fully saturated or fully unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{15}$;

$R^{15}$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 0, 1, 2, 3 or 4.

17. A compound or a stereoisomer or pharmaceutically acceptable salt thereof, selected from:

N-(4-((3-(2-(methylamino)-4-pyrimidinyl)-2-pyridinyl)oxy)-1-naphthalenyl)-1H-benzimidazol-2-amine;

N-(4-((3-(2-(methylamino)-4-pyrimidinyl)-2-pyridinyl)oxy)-1-naphthalenyl)-5-(trifluoromethyl)-1H-benzimidazol-2-amine;

N-(4-((3-(4-(methylamino)-1,3,5-triazin-2-yl)-2-pyridinyl)oxy)-1-naphthalenyl)-1H-benzimidazol-2-amine;

N-(4-((3-(2-(methylamino)-4-pyrimidinyl)-2-pyridinyl)oxy)-1-naphthalenyl)-1,3-benzoxazol-2-amine;

N-(4-((3-(2-(methylamino)-4-pyrimidinyl)-2-pyridinyl)oxy)-1-naphthalenyl)-1,3-benzothiazol-2-amine;

5,6-difluoro-N-(4-((3-(2-(methylamino)-4-pyrimidinyl)-2-pyridinyl)oxy)-1-naphthalenyl)-1H-benzimidazol-2-amine;

4-methyl-N-(4-((3-(2-(methylamino)-4-pyrimidinyl)-2-pyridinyl)oxy)-1-naphthalenyl)-1H-benzimidazol-2-amine;

N-(4-((3-(2-((2-(4-morpholinyl)ethyl)amino)-4-pyrimidinyl)-2-pyridinyl)oxy)-1-naphthalenyl)-1H-benzimidazol-2-amine;

6-chloro-5-fluoro-N-(4-((3-(2-(methylamino)-4-pyrimidinyl)-2-pyridinyl)oxy)-1-naphthalenyl)-1H-benzimidazol-2-amine;

N-(4-((3-(2-(methylsulfanyl)-4-pyrimidinyl)-2-pyridinyl)oxy)-1-naphthalenyl)-1H-benzimidazol-2-amine;

N~1~-(4-(2-((4-(1H-benzimidazol-2-ylamino)-1-naphthalenyl) oxy)-3-pyridinyl)-2-pyrimidinyl)-N~2~,N~2~-dimethyl-1,2-ethanediamine;

N~1~-(4-(2-((4-(1H-benzimidazol-2-ylamino)-1-naphthalenyl) oxy)-3-pyridinyl)-2-pyrimidinyl)-N~3~,N~3~-dimethyl-1,3-propanediamine;

N-(4-((3-(2-(methylsulfonyl)-4-pyrimidinyl)-2-pyridinyl)oxy)-1-naphthalenyl)-1H-benzimidazol-2-amine;

5,7-difluoro-N-(4-((3-(2-(methylamino)-4-pyrimidinyl)-2-pyridinyl)oxy)-1-naphthalenyl)-1H-benzimidazol-2-amine;

N-(1-(4-(2-((4-(1H-benzimidazol-2-ylamino)-1-naphthalenyl) oxy)-3-pyridinyl)-2-pyrimidinyl)-N-4-,N-4-dimethyl-1,4-butanediamine;

N-(4-((3-(2-(methylamino)-4-pyrimidinyl)-2-pyridinyl)oxy)-1-naphthalenyl)-5,7-bis(trifluoromethyl)-1H-benzimidazol-2-amine;

N-(4-((3-(2-(methylamino)-4-pyrimidinyl)-2-pyridinyl)oxy)-1-naphthalenyl)-3H-imidazo[4,5-b]pyridin-2-amine;

N-(4-((3-(2-(methylamino)-4-pyrimidinyl)-2-pyridinyl) oxy)-1-naphthalenyl)-3H-imidazo[4,5-c]pyridin-2-amine;

1-(3-(dimethylamino)propyl)-N-(4-((3-(2-(methylamino)-4-pyrimidinyl)-2-pyridinyl)oxy)-1-naphthalenyl)-1H-benzimidazol-2-amine;

1-(2-(dimethylamino)ethyl)-N-(4-((3-(2-(methylamino)-4-pyrimidinyl)-2-pyridinyl) oxy)-1-naphthalenyl)-1H-benzimidazol-2-amine;

N-(4-((3-(2-((3-(1-pyrrolidinyl)propyl)amino)-4-pyrimidinyl)-2-pyridinyl)oxy)-1-naphthalenyl)-1H-benzimidazol-2-amine;

N-(3-methyl-4-((3-(2-(methylamino)-4-pyrimidinyl)-2-pyridinyl)oxy)-1-naphthalenyl)-1H-benzimidazol-2-amine;

N-(3,5-dichloro-4-((3-(2-(methylamino)-4-pyrimidinyl)-2-pyridinyl)oxy)phenyl)-1H-benzimidazol-2-amine;

N-1H-benzimidazol-2-yl-8-((3-(2-(methylamino)-4-pyrimidinyl)-2-pyridinyl)oxy)-5-quinolinamine;

4,5-difluoro-N-(4-((3-(2-(methylamino)-4-pyrimidinyl)-2-pyridinyl)oxy)-1-naphthalenyl)-1H-benzimidazol-2-amine;

6,7-difluoro-N-(6-((3-(2-(methylamino)-4-pyrimidinyl)-2-pyridinyl)oxy)-3-pyridinyl)-1H-benzimidazol-2-amine;

N-(4-((2-(2-(methylamino)-4-pyrimidinyl)phenyl)oxy) phenyl)-1H-benzimidazol-2-amine;

6,7-difluoro-N-(4-((2-(2-(methylamino)-4-pyrimidinyl) phenyl) oxy)phenyl)-1H-benzimidazol-2-amine;

2-((4-(1H-benzimidazol-2-ylamino) phenyl)oxy)-N-methyl-3,4'-bipyridin-2'-amine;

2-((4-((6,7-difluoro-1H-benzimidazol-2-yl)amino)phenyl)oxy)-N-methyl-3,4'-bipyridin-2'-amine;

N-(4-((3-(2-amino-4-pyrimidinyl)-2-pyridinyl)oxy)-3-methyl-1-naphthalenyl)-1H-benzimidazol-2-amine;

N-(4-((3-(2-((2-(1-methyl-2-pyrrolidinyl)ethyl)amino)-4-pyrimidinyl)-2-pyridinyl)oxy)-1-naphthalenyl)-1H-benzimidazol-2-amine;

5,7-dimethyl-N-(3-methyl-4-((3-(4-pyrimidinyl)-2-pyridinyl) oxy)phenyl)-1,3-benzoxazol-2-amine;

6-methyl-N-(3-methyl-4-((3-(4-pyrimidinyl)-2-pyridinyl) oxy)phenyl)-1,3-benzoxazol-2-amine;

5-methyl-N-(3-methyl-4-((3-(4-pyrimidinyl)-2-pyridinyl) oxy)phenyl)-1,3-benzoxazol-2-amine;

4-methyl-N-(3-methyl-4-((3-(4-pyrimidinyl)-2-pyridinyl) oxy)phenyl)-1,3-benzoxazol-2-amine;

N-(4-((3-(2-(((1-ethyl-4-piperidinyl)methyl)amino)-4-pyrimidinyl)-2-pyridinyl)oxy)-1-naphthalenyl)-1H-benzimidazol-2-amine;

N-(4-((3-(2-((1-methyl-4-piperidinyl)amino)-4-pyrimidinyl)-2-pyridinyl)oxy)-1-naphthalenyl)-1H-benzimidazol-2-amine 4,5-difluoro-N-(4-((3-(1H-pyrazol-4-yl)-2-pyridinyl)oxy) phenyl)-1H-benzimidazol-2-amine;

N-(4-((3-(1H-pyrazol-4-yl)-2-pyridinyl)oxy)phenyl)-1H-benzimidazol-2-amine;

N-(4-((3-(2-amino-4-pyrimidinyl)-2-pyridinyl)oxy)phenyl)-4,5-difluoro-1H-benzimidazol-2-amine;

N-(6-((3-(2-amino-4-pyrimidinyl)-2-pyridinyl)oxy)-3-pyridinyl)-6,7-difluoro-1H-benzimidazol-2-amine;

N-(4-((3-(2-(methylamino)-4-pyrimidinyl)-2-pyridinyl) oxy)phenyl)-1,3-benzoxazol-2-amine;

N-(4-((3-(2-(methylamino)-4-pyrimidinyl)-2-pyridinyl) oxy)phenyl)-1H-benzimidazol-2-amine;

N-(3-methyl-4-((3-(2-(methylamino)-4-pyrimidinyl)-2-pyridinyl)oxy)phenyl)-1,3-benzoxazol-2-amine;

N-(3-methyl-4-((3-(2-(methylamino)-4-pyrimidinyl)-2-pyridinyl)oxy)phenyl)-1H-benzimidazol-2-amine;

N-(4-((3-(2-(methylamino)-4-pyrimidinyl)-2-pyridinyl) oxy)phenyl)-1,3-benzothiazol-2-amine;

5-methyl-N-(4-((3-(2-(methylamino)-4-pyrimidinyl)-2-pyridinyl)oxy)phenyl)-1H-benzimidazol-2-amine;

N-(4-((3-(2-(methylamino)-4-pyrimidinyl)-2-pyridinyl) oxy)phenyl)-5-(trifluoromethyl)-1H-benzimidazol-2-amine;

5-methyl-N-(3-methyl-4-((3-(2-(methylamino)-4-pyrimidinyl)-2-pyridinyl)oxy)phenyl)-1H-benzimidazol-2-amine;

N-(3-methyl-4-((3-(2-(methylamino)-4-pyrimidinyl)-2-pyridinyl)oxy)phenyl)-5-(trifluoromethyl)-1H-benzimidazol-2-amine;

1-methyl-N-(3-methyl-4-((3-(2-(methylamino)-4-pyrimidinyl)-2-pyridinyl)oxy)phenyl)-1H-benzimidazol-2-amine;

1-methyl-N-(4-((3-(2-(methylamino)-4-pyrimidinyl)-2-pyridinyl)oxy)phenyl)-1H-benzimidazol-2-amine;

1-methyl-N-(4-((3-(2-(methylamino)-4-pyrimidinyl)-2-pyridinyl)oxy)phenyl)-5-(trifluoromethyl)-1H-benzimidazol-2-amine;

5,6-difluoro-N-(4-((3-(2-(methylamino)-4-pyrimidinyl)-2-pyridinyl)oxy)phenyl)-1H-benzimidazol-2-amine;

5-(1,1-dimethylethyl)-N-(4-((3-(2-(methylamino)-4-pyrimidinyl)-2-pyridinyl)oxy)phenyl)-1H-benzimidazol-2-amine;

6-chloro-5-fluoro-N-(4-((3-(2-(methylamino)-4-pyrimidinyl)-2-pyridinyl)oxy)phenyl)-1H-benzimidazol-2-amine;

4-methyl-N-(4-((3-(2-(methylamino)-4-pyrimidinyl)-2-pyridinyl)oxy)phenyl)-1H-benzimidazol-2-amine;

5-fluoro-N-(4-((3-(2-(methylamino)-4-pyrimidinyl)-2-pyridinyl)oxy)phenyl)-1H-benzimidazol-2-amine;

4-methyl-N-(3-methyl-4-((3-(2-(methylamino)-4-pyrimidinyl)-2-pyridinyl)oxy)phenyl)-1H-benzimidazol-2-amine;

5-fluoro-N-(3-methyl-4-((3-(2-(methylamino)-4-pyrimidinyl)-2-pyridinyl)oxy)phenyl)-1H-benzimidazol-2-amine;

5,6-difluoro-N-(3-methyl-4-((3-(2-(methylamino)-4-pyrimidinyl)-2-pyridinyl)oxy)phenyl)-1H-benzimidazol-2-amine;

6-chloro-5-fluoro-N-(3-methyl-4-((3-(2-(methylamino)-4-pyrimidinyl)-2-pyridinyl)oxy)phenyl)-1H-benzimidazol-2-amine;

N-(2-methyl-4-((3-(2-(methylamino)-4-pyrimidinyl)-2-pyridinyl)oxy)phenyl)-1H-benzimidazol-2-amine;

N-(2,3-dimethyl-4-((3-(2-(methylamino)-4-pyrimidinyl)-2-pyridinyl)oxy)phenyl)-1H-benzimidazol-2-amine;

5,6-dimethyl-N-(4-(3-(2-(methylamino)pyramidin-4-yl) pyridin-2-yloxy)phenyl)-1H-benzo[d]imidazol-2-amine;

4,6-difluoro-N-(4-((3-(2-(methylamino)-4-pyrimidinyl)-2-pyridinyl)oxy)phenyl)-1H-benzimidazol-2-amine;

4,5-dimethyl-N-(4-((3-(2-(methylamino)-4-pyrimidinyl)-2-pyridinyl)oxy)phenyl)-1H-benzimidazol-2-amine;

5-fluoro-N-(4-((3-(2-((3-(4-morpholinyl)propyl)amino)-4-pyrimidinyl)-2-pyridinyl)oxy)phenyl)-1H-benzimidazol-2-amine;

5,6-dichloro-N-(4-((3-(2-(methylamino)-4-pyrimidinyl)-2-pyridinyl)oxy)phenyl)-1H-benzimidazol-2-amine;

N-(4-((3-(2-(methylamino)-4-pyrimidinyl)-2-pyridinyl) oxy)phenyl)-4,6-bis(trifluoromethyl)-1H-benzimidazol-2-amine;

5-chloro-6-methyl-N-(4-((3-(2-(methylamino)-4-pyrimidinyl)-2-pyridinyl)oxy)phenyl)-1H-benzimidazol-2-amine;

5-fluoro-N-(4-((3-(2-((4-(4-methyl-1-piperazinyl)phenyl)amino)-4-pyrimidinyl)-2-pyridinyl)oxy)phenyl)-1H-benzimidazol-2-amine;

N-(4-((3-(2-(methylamino)-4-pyrimidinyl)-2-pyridinyl)oxy)phenyl)-5-(4-methyl-1-piperazinyl)-1H-benzimidazol-2-amine;

N'-(4-(2-((4-((5,6-difluoro-1H-benzimidazol-2-yl)amino)phenyl)oxy)-3-pyridinyl)-2-pyrimidinyl)-N,N-dimethyl-1,3-propanediamine;

4,5-difluoro-N-(4-((3-(2-(methylamino)-4-pyrimidinyl)-2-pyridinyl)oxy)phenyl)-1H-benzimidazol-2-amine;

N-(4-((3-(2-((3-(1-piperidinyl)propyl)amino)-4-pyrimidinyl)-2-pyridinyl)oxy)-1-naphthalenyl)-1H-benzimidazol-2-amine;

N'-(4-(2-((4-(1H-benzimidazol-2-ylamino)-1-naphthalenyl) oxy)-3-pyridinyl)-2-pyrimidinyl)-N,N,2,2-tetramethyl-1,3-propanediamine;

5,6-difluoro-N-(4-((3-(1H-pyrrolo[2,3-b]pyridin-4-yl)-2-pyridinyl)oxy)phenyl)-1H-benzimidazol-2-amine;

N-(4-((3-(2-((3-(1H-1,2,3-triazol-1-yl)propyl)amino)-4-pyrimidinyl)-2-pyridinyl)oxy)-1-naphthalenyl)-1H-benzimidazol-2-amine;

5,6-difluoro-N-(4-((3-(2-((3-(4-thiomorpholinyl)propyl)amino)-4-pyrimidinyl)-2-pyridinyl)oxy)phenyl)-1H-benzimidazol-2-amine;

N'-(4-(2-((4-((5,6-difluoro-1H-benzimidazol-2-yl)amino)phenyl)oxy)-3-pyridinyl)-2-pyrimidinyl)-N,N-dimethyl-1,4-butanediamine;

2,2'-((3-((4-(2-((4-((5,6-difluoro-1H-benzimidazol-2-yl)amino)phenyl)oxy)-3-pyridinyl)-2-pyrimidinyl)amino)propyl)imino)diethanol;

N'-(4-(2-((4-((5,6-difluoro-1H-benzimidazol-2-yl)amino)phenyl)oxy)-3-pyridinyl)-2-pyrimidinyl)-N,N-dimethyl-1,5-pentanediamine;

N'-(4-(2-((4-((5,6-difluoro-1H-benzimidazol-2-yl)amino)phenyl)oxy)-3-pyridinyl)-2-pyrimidinyl)-N,N-dimethyl-1,6-hexanediamine;

5,6-difluoro-N-(4-((3-(2-((3-(4-morpholinyl)propyl)amino)-4-pyrimidinyl)-2-pyridinyl)oxy)phenyl)-1H-benzimidazol-2-amine;

4,5,6-trifluoro-N-(4-(3-(2-(methylamino)pyrimidin-4-yl)pyridin-2-yloxy)phenyl)-1H-benzo[d]imidazol-2-amine;

N-(4-(3-(2-(methylamino)pyrimidin-4-yl)pyridin-2-yloxy)phenyl)-1H-thieno[3,4-d]imidazol-2-amine;

N-(4-((3-(1H-pyrrolo[2,3-b]pyridin-4-yl)-2-pyridinyl)oxy)phenyl)-1H-benzimidazol-2-amine;

N-(4-((3-(2-(methylamino)-4-pyrimidinyl)-2-pyridinyl)thio) phenyl)-1H-benzimidazol-2-amine;

4,5-difluoro-N-(4-((3-(1H-pyrrolo[2,3-b]pyridin-4-yl)-2-pyridinyl)oxy)phenyl)-1H-benzimidazol-2-amine;

4,5-difluoro-N-(4-((3-(2-(methylamino)-4-pyrimidinyl)-2-pyridinyl)thio)phenyl)-1H-benzimidazol-2-amine;

4,5-difluoro-N-(4-((3-(2-((4-(4-methyl-1-piperazinyl)phenyl)amino)-4-pyrimidinyl)-2-pyridinyl)oxy)phenyl)-1H-benzimidazol-2-amine;

4,5-difluoro-N-(4-((3-(2-(methylamino)-4-pyrimidinyl)-2-pyridinyl)oxy)-3-(methyloxy)phenyl)-1H-benzimidazol-2-amine N-(4-((3-(2-(methylamino)-4-pyrimidinyl)-2-pyridinyl)oxy)-3-(methyloxy)phenyl)-1H-benzimidazol-2-amine;

4,5-difluoro-N-(3-methyl-4-((3-(2-(methylamino)-4-pyrimidinyl)-2-pyridinyl)oxy)phenyl)-1H-benzimidazol-2-amine;

4,5,6,7-tetrafluoro-N-(4-((3-(2-(methylamino)-4-pyrimidinyl)-2-pyridinyl)oxy)phenyl)-1H-benzimidazol-2-amine;

4,5-difluoro-N-(2-fluoro-4-((3-(2-(methylamino)-4-pyrimidinyl)-2-pyridinyl)oxy)phenyl)-1H-benzimidazol-2-amine;

N-(4-((3-(2-(methylamino)-4-pyrimidinyl)-2-pyridinyl)oxy)phenyl)-1-phenyl-1H-benzimidazol-2-amine;

N-(3-chloro-4-((3-(2-(methylamino)-4-pyrimidinyl)-2-pyridinyl)oxy)phenyl)-4,5-difluoro-1H-benzimidazol-2-amine;

4-(2-((4-((4-methyl-1-phenyl-1H-pyrazol-3-yl)amino)phenyl) oxy)-3-pyridinyl)-2-pyrimidinamine;

N-(4-((3-(2-(methylamino)-4-pyrimidinyl)-2-pyridinyl)oxy)-1-naphthalenyl)-1H-benzimidazol-2-amine;

N-(4-((3-(2-(methylamino)-4-pyrimidinyl)-2-pyridinyl)oxy)-1-naphthalenyl)-5-(trifluoromethyl)-1H-benzimidazol-2-amine;

N-(4-((3-(4-(methylamino)-1,3,5-triazin-2-yl)-2-pyridinyl) oxy)-1-naphthalenyl)-1H-benzimidazol-2-amine;

N-(4-((3-(2-(methylamino)-4-pyrimidinyl)-2-pyridinyl)oxy)-1-naphthalenyl)-1,3-benzoxazol-2-amine;

N-(4-((3-(2-(methylamino)-4-pyrimidinyl)-2-pyridinyl)oxy)-1-naphthalenyl)-1,3-benzothiazol-2-amine;

5,6-difluoro-N-(4-((3-(2-(methylamino)-4-pyrimidinyl)-2-pyridinyl)oxy)-1-naphthalenyl)-1H-benzimidazol-2-amine;

4-methyl-N-(4-((3-(2-(methylamino)-4-pyrimidinyl)-2-pyridinyl)oxy)-1-naphthalenyl)-1H-benzimidazol-2-amine;

N-(4-((3-(2-((2-(4-morpholinyl)ethyl)amino)-4-pyrimidinyl)-2-pyridinyl)oxy)-1-naphthalenyl)-1H-benzimidazol-2-amine;

6-chloro-5-fluoro-N-(4-((3-(2-(methylamino)-4-pyrimidinyl)-2-pyridinyl)oxy)-1-naphthalenyl)-1H-benzimidazol-2-amine; and N-(4-((3-(2-(methylsulfanyl)-4-pyrimidinyl)-2-pyridinyl)oxy)-1-naphthalenyl)-1H-benzimidazol-2-amine.

18. A pharmaceutical composition comprising a pharmaceutically acceptable carrier and the compound of claim 1.

19. A method of treating breast cancer or rheumatoid arthritis in a subject, the method comprising administering to the subject an effective dosage amount of the compound of claim 1.

20. A method of making a compound of claim 1, the method comprising the step of reacting compound of Formula A

A

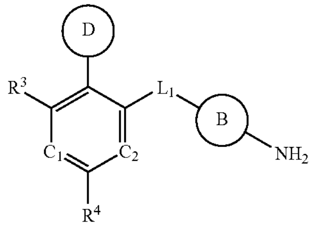

with a compound of Formula B
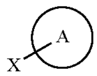
B
wherein A, B, $C^1$, $C^2$, D, $L^1$, $L^2$ and $R^{3-4}$ are defined in claim 1 and X is a halogen, to make a compound of Formula I.
21. A pharmaceutical composition comprising a pharmaceutically acceptable carrier and the compound of claim 13.
22. A pharmaceutical composition comprising a pharmaceutically acceptable carrier and the compound of claim 16.
* * * * *